US008476419B2

(12) United States Patent (10) Patent No.: US 8,476,419 B2
Thielemans et al. (45) Date of Patent: Jul. 2, 2013

(54) ENHANCING THE T-CELLS STIMULATORY CAPACITY OF HUMAN ANTIGEN PRESENTING CELLS AND THEIR USE IN VACCINATION

(75) Inventors: Kris Maria Magdalena Thielemans, Wilrijk (BE); Aude Bonehill, Essene (BE)

(73) Assignee: Vrije Universiteit Brussel, Brussel (BE)

( * ) Notice: Subject to any disclaimer, the term of this patent is extended or adjusted under 35 U.S.C. 154(b) by 315 days.

(21) Appl. No.: 12/677,476

(22) PCT Filed: Sep. 12, 2008

(86) PCT No.: PCT/EP2008/062174
§ 371 (c)(1),
(2), (4) Date: Mar. 10, 2010

(87) PCT Pub. No.: WO2009/034172
PCT Pub. Date: Mar. 19, 2009

(65) Prior Publication Data
US 2010/0215674 A1 Aug. 26, 2010

(30) Foreign Application Priority Data
Sep. 14, 2007 (WO) .................. PCT/EP2007/059732

(51) Int. Cl.
*C07H 21/04* (2006.01)
*C12N 15/00* (2006.01)

(52) U.S. Cl.
USPC ......................................... 536/23.5; 435/455

(58) Field of Classification Search
None
See application file for complete search history.

(56) References Cited

U.S. PATENT DOCUMENTS

| 6,969,609 | B1 * | 11/2005 | Schlom et al. | 435/325 |
|---|---|---|---|---|
| 2004/0146492 | A1 * | 7/2004 | Hwu et al. | 424/93.21 |
| 2006/0034810 | A1 * | 2/2006 | Riley et al. | 424/93.21 |

FOREIGN PATENT DOCUMENTS

| WO | WO 2005/012509 | 2/2005 |
|---|---|---|
| WO | WO 2006/042177 | 4/2006 |
| WO | WO 2007/078196 | 7/2007 |

OTHER PUBLICATIONS

Abdel-Wahab et al., 2005, J. Surg. Res. vol. 124: 264-273.*
Abdel-Wahab, et al., "Cotransfection of DC with TLR4 and MART-1 RNA Induces MART-1 Specific Responses," *Journal of Surgical Research*, vol. 124, No. 2, pp. 264-273, Apr. 2005.
Bonehill, et al. "Enhancing the T-cell Stimulatory Capacity of Human Dendritic Cells by Co-electroporation with CD40L, CD70 and Constitutively active TLR4 Encoding mRNA," *Molecular Therapy*, vol. 16, No. 6, pp. 1170-1180, Jun. 2008.
Liu, et al. "Adenovirus-mediated CD40 Ligand Gene-engineered Dendritic Cells Elicit Enhanced CD8+ Cytotoxic T-cell Activation and Antitumor Immunity," *Cancer Gene Therapy*, vol. 9, pp. 202-208, 2002.
Tuyaerts, et al. "Current Approaches in Dendritic Cell Generation and Future Implications for Cancer Immunotherapy," *Cancer Immunology Immunotherapy*, vol. 56, No. 10, pp. 1513-1537, May 15, 2007.
International Search Report dated Dec. 30, 2008 and issued to priority international application No. PCT/EP2008/062174.
Croft, "Control of Immunity by the TNFR-related Molecule OX40 (CD134)," *The Annual Review of Immunology*, vol. 28, pp. 57-78, 2010.
Hori, "Developmental Plasticity of Foxp3+ regulatory T Cells," *Current Opinion in Immunology*, vol. 22, pp. 575-582, 2010.
Hori, "Regulatory T Cell Plasticity: Beyond the Controversies," *Trends in Immunology* vol. 32, No. 7, pp. 295-300, Jul. 2011.
Jonuleit, et al. "Pro-inflammatory Cytokines and Prostaglandins Induce Maturation of Potent Immunostimulatory Dendritic Cells under Fetal Calf Serum-free Conditions," *European Journal of Immunology*, vol. 27, No. 12, pp. 3135-3142, Dec. 1997.
Koch, et al. "T-bet Controls Regulatory T Cell Homeostasis and Function During Type-1 Inflammation," *Nature Immunology*, vol. 10, No. 6, pp. 595-602, Jun. 2009.
Kubo, et al. "Regulatory T Cell Suppression and Anergy are Differentially Regulated by Proinflammatory Cytokines Produced by TLR-activated Dendritic Cells," *The Journal of Immunology*, vol. 173, pp. 7249-7258, 2004.
McClymont, et al. "Plasticity of Human Regulatory T Cells in Healthy Subjects and Patients with Type 1 Diabetes," *The Journal of Immunology*, vol. 186, pp. 3918-3926, Mar. 2011.
Oldenhove, et al. "Decrease of Foxp3+ Treg Cell Number and Acquisition of Effector Cell Phenotype During Lethal Infection," *Immunity*, vol. 31, No. 5, 29 pages, Nov. 20, 2009, Author Manuscript.
Pasare, et al. "Toll Pathway-dependent Blockade of $CD4^+CD25^+$ T Cell-mediated Suppression by Dendritic Cells," *Science*, vol. 299, pp. 1033-1036, Feb. 14, 2003.
Ramirez-Montagut, et al. "Glucocorticoid-induced TMF Receptor Family Related Gene Activation Overcomes Tolerance/Ignorance to Melanoma Differentiation Antigens and Enhances Antitumor Immunity," *The Journal of Immunology*, vol. 176, pp. 6434-6442, 2006.
Stephens, et al. "Engagement of Glucocorticoid-induced TNFR Family-related Receptor on Effector T Cells by its Ligand Mediates Resistance to Suppression by $CD4^+CD25^+$ T Cells," *The Journal of Immunology*, vol. 173, pp. 5008-5020, 2004.

(Continued)

*Primary Examiner* — Amy Juedes
(74) *Attorney, Agent, or Firm* — Knobbe, Martens, Olson & Bear LLP

(57) ABSTRACT

With the current invention, we provide new methods of enhancing the T-cell stimulatory capacity of human dendritic cells (DCs) and their use in cancer vaccination. The method comprises the introduction of different molecular adjuvants to human DCs through transfection with at least two mRNA or DNA molecules encoding markers selected from the group of: CD40L, CD70, constitutively active TLR4 (caTLR4), IL-12p70, EL-selectin, CCR7 and/or 4-1 BBL; or in combination with inhibition of SOCS, A20, PD-L1 and/or STAT3 expression, for example through siRNA transfection. We could show a clear increase in the immunostimulatory capacity of DCs obtained in this way, enabling them to elicit an unexpectedly high T-cell immune response in vitro. Introduction of at least two of the above molecules, in combination with a tumor-specific antigen enables the DCs to elicit a significant host-mediated T-cell immune response in vivo against the tumor antigen and thus makes them very attractive in the manufacturing of anti-cancer vaccines.

9 Claims, 16 Drawing Sheets

OTHER PUBLICATIONS

Warger, et al. "Synergistic Activation of Dendritic Cells by Combined Toll-like Receptor Ligation Induces Superior CTL Responses in vivo," *Blood*, vol. 108, No. 2, pp. 544-550, Jul. 15, 2006.

Wei, et al. "Global Mapping of H3K4me3 and H3K27me3 Reveals Specificity and Plasticity in Lineage Fate Determination of Differentiating CD4+ T Cells," *Immunity* 30, pp. 155-167, Jan. 16, 2009.

Zhou, et al. "TGF-β-induced Foxp3 Inhibits $T_H17$ Cell Differentiation by Antagonizing RORγt Function," *Nature*, vol. 453, pp. 236-241, May 8, 2008.

Wilgenhof S, Van Nuffel AM, Corthals J, Heirman C, Tuyaerts S, Benteyn D, De Coninck A, Van Riet I, Verfaillie G, Vandeloo J, Bonehill A, Thielemans K, Neyns B. J. *Therapeutic vaccination with an autologous mRNA electroporated dendritic cell vaccine in patients with advanced melanoma*. Immunother. Jun. 2011; 34(5):448-56.

* cited by examiner

CD40L expression

CD70 expression

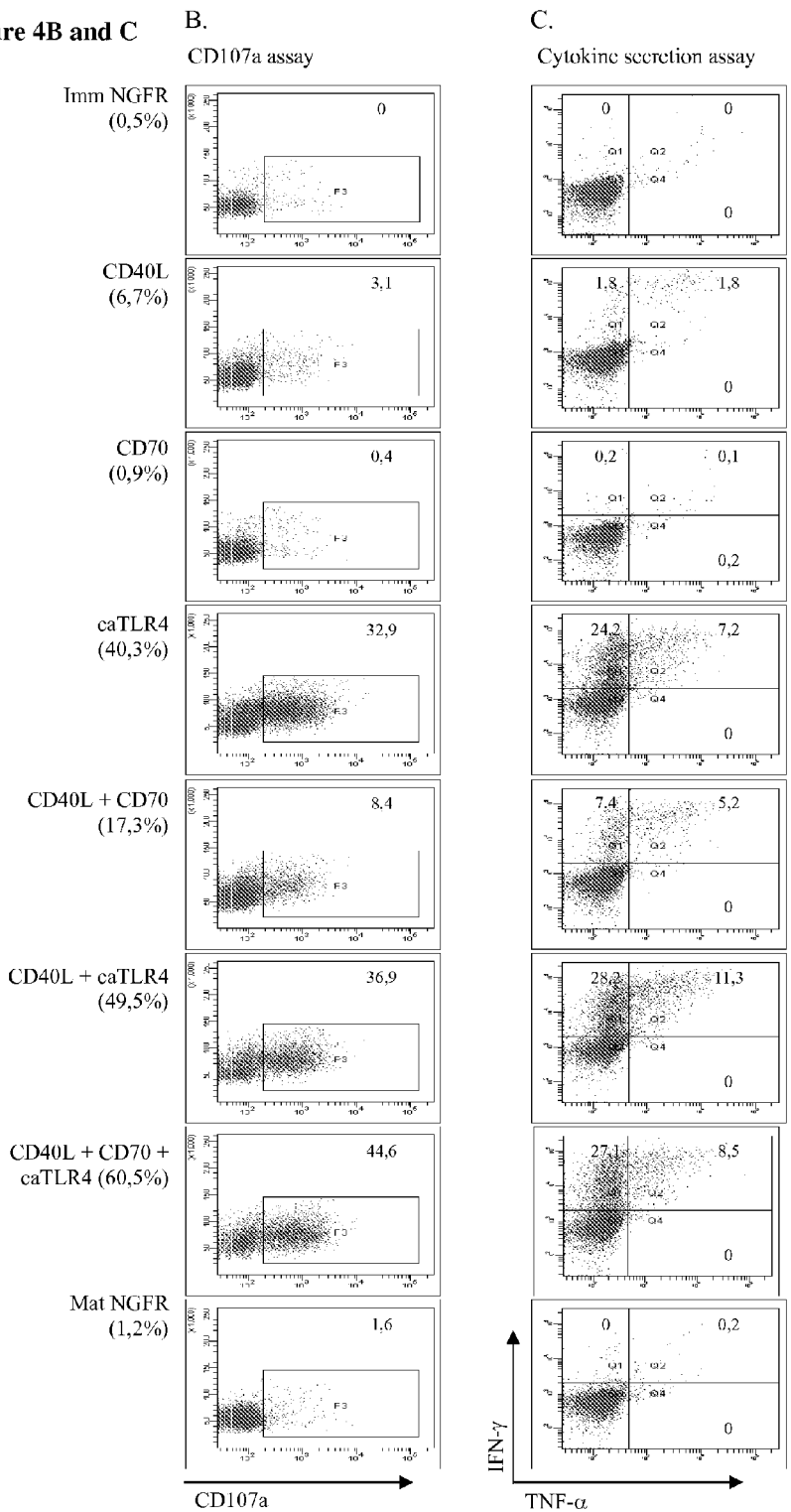
Figure 4B and C

Figure 6B and C
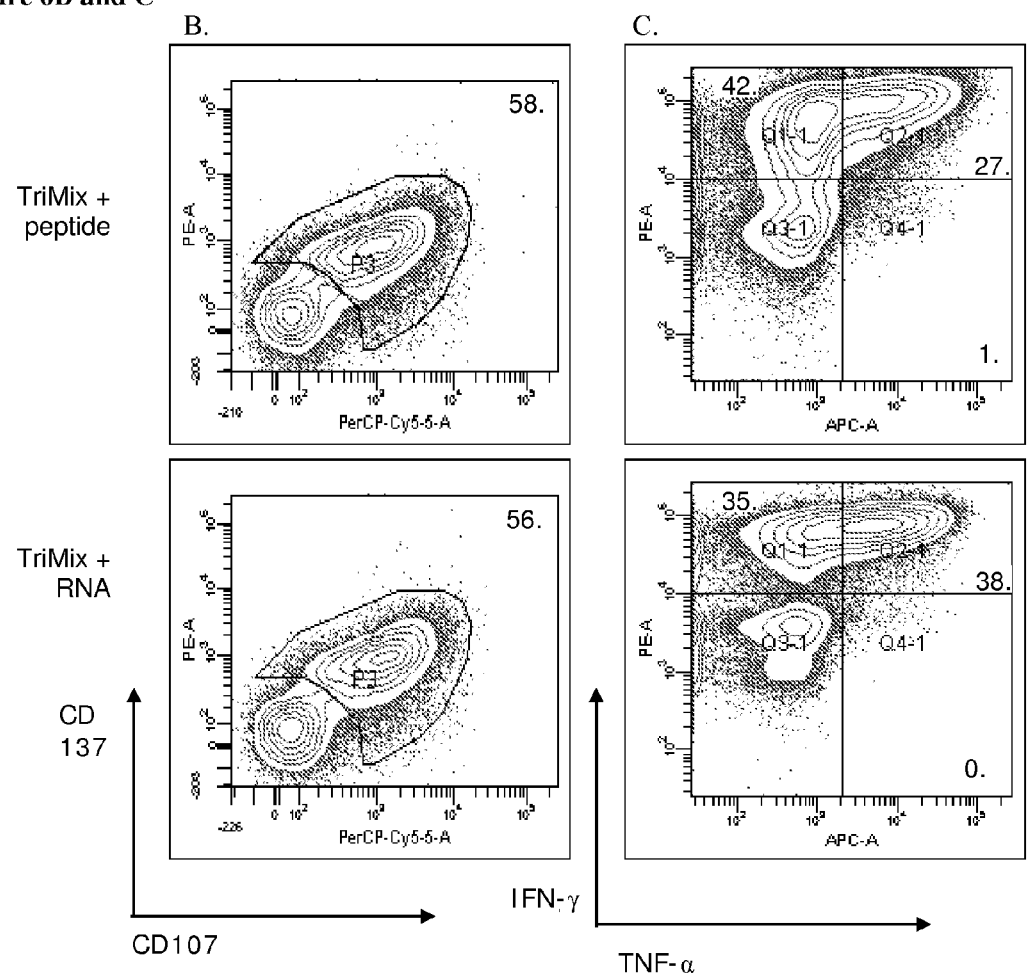

SEQUENCE LISTING

```
<160> NUMBER OF SEQ ID NOS: 8

<210> SEQ ID NO 1
<211> LENGTH: 34
<212> TYPE: DNA
<213> ORGANISM: Artificial
<220> FEATURE:
<223> OTHER INFORMATION: primer

<400> SEQUENCE: 1
aaaaagcttc caccatggca cggccacatc cctg                              34

<210> SEQ ID NO 2
<211> LENGTH: 27
<212> TYPE: DNA
<213> ORGANISM: Artificial
<220> FEATURE:
<223> OTHER INFORMATION: primer

<400> SEQUENCE: 2
cccctcgagt caggggagc aggcagg                                       27

<210> SEQ ID NO 3
<211> LENGTH: 30
<212> TYPE: DNA
<213> ORGANISM: Artificial
<220> FEATURE:
<223> OTHER INFORMATION: primer

<400> SEQUENCE: 3
gatggatccg tcatgatcga aacatacaac                                   30

<210> SEQ ID NO 4
<211> LENGTH: 27
<212> TYPE: DNA
<213> ORGANISM: Artificial
<220> FEATURE:
<223> OTHER INFORMATION: primer

<400> SEQUENCE: 4
cggtacccat cagagtttga gtaagcc                                      27
```

```
<210> SEQ ID NO 5
<211> LENGTH: 30
<212> TYPE: DNA
<213> ORGANISM: Artificial
<220> FEATURE:
<223> OTHER INFORMATION: primer

<400> SEQUENCE: 5
aaaagcttcc accatgccgg aggagggttc                                30

<210> SEQ ID NO 6
<211> LENGTH: 27
<212> TYPE: DNA
<213> ORGANISM: Artificial
<220> FEATURE:
<223> OTHER INFORMATION: primer

<400> SEQUENCE: 6 gggggaatt ctcaggggcg cacccac                                    27

<210> SEQ ID NO 7
<211> LENGTH: 30
<212> TYPE: DNA
<213> ORGANISM: Artificial
<220> FEATURE:
<223> OTHER INFORMATION: primer

<400> SEQUENCE: 7
ggggatcctg tgctgagttt gaatatcacc                                30

<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8
gggaattctc agatagatgt tcttcctg                                  28
```

ENHANCING THE T-CELLS STIMULATORY CAPACITY OF HUMAN ANTIGEN PRESENTING CELLS AND THEIR USE IN VACCINATION

CROSS-REFERENCE TO RELATED APPLICATIONS

This application is the U.S. National Phase under 35 U.S.C. §371 of International Application PCT/EP2008/062174, filed Sept. 12, 2008, which claims priority to PCT/EP2007/059732, filed Sept. 14, 2007.

FIELD OF THE INVENTION

The invention is situated in the field of immunotherapy using antigen presenting cells from a patient modified such that they are capable of presenting a target-specific antigen in the patient, leading to a host-mediated immune response to the target-expressing cells. The invention is especially related to increasing the immunostimulatory effect of the antigen presenting cells in view of vaccination of patients suffering from cancer or infectious disorders.

BACKGROUND OF THE INVENTION

Over the years, antigen presenting cells such as Dendritic Cells (DCs) have emerged as key players in orchestrating immune responses and in particular in inducing primary responses in patients in general. Nowadays, DCs can be generated on a large scale in closed systems, yielding sufficient numbers of cells for use in clinical trials. Simultaneously, antigens derived from infectious microorganisms and many different tumor-associated antigens which are either selectively or preferentially expressed by tumor cells have been identified. Also, a whole range of strategies to load DCs with such antigens have been designed. Together, these findings enabled the start of clinical studies with antigen-loaded DC in cancer patients and in patients suffering from infections. Nonetheless, satisfying immunological responses and clinical outcomes have not been achieved so far.

One major problem using DCs loaded with a target-specific antigen as antigen-presenting cells (APCs) is that they are insufficient in eliciting a strong immune response both in vitro and in vivo. One cause of this insufficient immunostimulation is the complicated in vitro manipulation of the DCs prior to their use, leading to loss of their characteristic properties such as secretion of cytokines and other factors triggering immune responses. Another problem is that artificially made DCs often do not express the necessary cellular markers on their cell-surface needed to activate a T-cell response to the target-specific antigen presented by the DCs thereby overcoming the often occurring T-cell tolerance towards the target-specific antigens.

It is therefore the object of the current invention to provide a solution to the above stated problems.

SUMMARY OF THE INVENTION

The inventors have established that the T cell stimulatory capacity of antigenic-peptide pulsed antigen presenting cells or antigen presenting cells (co-)electroporated with an mRNA encoding a target-specific antigen can be greatly enhanced by providing them with three different molecular adjuvants through electroporation with a mixture of mRNA or DNA molecules encoding two or more immunostimulatory factors.

The invention provides the proof of concept that such modified antigen presenting cells pulsed with a target-specific peptide or co-electroporated with mRNA encoding a target-specific antigen can stimulate antigen-specific T cells both in vitro and after vaccination and thus form a promising new approach for anti-tumor, anti-viral, anti-bacterial or anti-fungal immunotherapy.

The invention thus provides for a method for improving the immunostimulatory characteristics of antigen presenting cells comprising the simultaneous introduction of at least two different mRNA or DNA molecules encoding proteins that modify the functionality of the APCs, characterized in that amongst the functional proteins at least two antigens are introduced, selected from the group comprising CD40L, CD70, caTLR4, IL-12p70, EL-selectin, CCR7, and/or 4-1BBL; or in combination with molecules inhibiting SOCS, A20, PD-L1 or STAT3 expression or function. In a specific embodiment, the antigen-specific stimulations are performed without the addition of any exogenous IL-2 and/or IL-7 to support T-cell proliferation and survival. In certain embodiments, the antigen presenting cells are additionally stimulated with soluble factors selected from the group comprising TLR ligands, IFN-gamma, TNF-alpha, IL-6, IL-1 beta and/or PGE2.

Preferably, the method used for simultaneous introduction of at least two different mRNA or DNA molecules is selected from the group of electroporation, viral transduction, lipofection and transfection of mRNA or DNA encoding the immunostimulatory antigens.

The invention further provides a method for preparing an immunotherapy agent comprising the steps of:
a) obtaining or providing antigen presenting cells,
b) in vitro modifying said pool of antigen presenting cells of
  step a) with at least 2 immunostimulatory antigens selected
  from the group comprising CD40L, CD70, caTLR4,
  IL-12p70, EL-selectin, CCR7, and/or 4-1BBL; and/or
  SOCS, A20, PD-L1 or STAT3 inhibition, and
c) in vitro modifying the pool of antigen presenting cells from
  step b) such that they present target-specific antigen
  derived epitopes.

In preferred embodiments, the method of modification used in step b) and/or c) is selected from the group of electroporation, viral transduction, lipofection or transfection of mRNA or DNA encoding the immunostimulatory antigens.

Preferably, the specific immunostimulatory proteins and the target antigens are introduced through a one-step mechanism. In a preferred embodiment, co-electroporation of the mRNA or DNA encoding a target-specific antigen with the mRNA or DNA encoding the immunostimulatory factors, is used.

In another embodiment, protein or peptide pulsing is used to load the target-specific antigen or its derived antigenic peptides onto the antigen presenting cells.

A preferred combination of immunostimulatory factors used in the methods of the invention is CD40L and CD70. In other preferred embodiments, the combination of CD40L, CD70 and caTLR4 immunostimulatory molecules is used, which is called the "TriMix" hereinafter.

The antigen presenting cells used in the methods of the invention are selected from the group consisting of patient-specific dendritic cells (DCs) or B-cells; or established dendritic cell lines or B-cell lines.

The invention further provides a vaccine comprising the immunotherapy agent obtained by any of the methods of the invention mentioned above, further comprising pharmaceutically acceptable adjuvant(s).

In a specific embodiment, the immunotherapy agent is directed to a target-specific antigen which can be a tumor antigen, or a bacterial, viral or fungal antigen. Said target-specific antigen can be derived from either one of: total mRNA isolated from (a) target cell(s), one or more specific target mRNA molecules, protein lysates of (a) target cell(s), specific proteins from (a) target cell(s), or a synthetic target-specific peptide or protein and synthetic mRNA or DNA encoding a target-specific antigen or its derived peptides.

The invention further encompasses the use of a preparation of antigen presenting cells obtained by the method of the invention or the immunotherapy agent obtained by the method of the invention in the manufacture of a vaccine capable of eliciting an immune response in a patient in need thereof.

The invention further provides for a method to screen for new target-specific epitopes that can be used for vaccination of patients, using antigen presenting cells obtained by the immunostimulation method of the invention comprising;
   a) stimulating T cells from healthy donors or patients (previously vaccinated or not with an anti-target vaccine) with antigen presenting cells obtained by the immunostimulation method of the invention;
   b) identifying T cells specific for the used target-antigen; and
   c) identifying the target-antigen derived epitope for which the T cell is specific.

In addition, the invention provides for a method of following the effects of the treatment with an anti-target vaccine in a patient; comprising the detection and analysis of the immune response towards the target-specific antigen elicited in the subject previously injected with the anti-target vaccine obtained by any of the methods of the invention. In preferred embodiments, the patient is suffering from a disease or disorder selected from the group of: cancer, bacterial, viral or fungal infection, e.g. HIV infection or hepatitis.

The invention also provides a kit for improving the immunostimulatory characteristics of antigen presenting cells comprising a combination of at least two different mRNA or DNA molecules encoding functional immunostimulatory proteins selected from the group consisting of CD40L, CD70, caTLR4, IL-12p70, EL-selectin, CCR7, and/or 4-1BBL, and optionally comprising molecules inhibiting SOCS, A20, PD-L1 or STAT3 expression or function. In a preferred embodiment, the kit comprises mRNA or DNA molecules encoding CD40L and CD70. In a more preferred embodiment, the kit of the invention can additionally comprise the mRNA or DNA encoding for the caTLR4, resulting in the so-called "TriMix". In certain embodiments, the kit of the invention comprises a single mRNA or DNA molecule, wherein said two or more mRNA or DNA molecules encoding the immunostimulatory proteins are combined. Preferably, the single mRNA or DNA molecule is capable of expressing the two or more immunostimulatory proteins simultaneously e.g. the two or more mRNA or DNA molecules encoding the immunostimulatory proteins are linked in the single mRNA or DNA molecule by an internal ribosomal entry site (IRES) or a self-cleaving 2a peptide encoding sequence.

In addition, the invention provides an ex vivo method of amplifying antigen-specific T-cells from a patient. The patient can be previously vaccinated or not. The amplified pool of T-cells can then be used for new or additional vaccination (boosting) of the patient. The invention thus provides a method for the ex-vivo amplification of a pool of T-cells from a patient comprising;

a) obtaining T-cells from a patient which was vaccinated prior to the isolation or not
b) bringing the T-cells into contact with the immunotherapy agent of the invention, comprising antigen-presenting cells of the invention, and
c) identifying, isolating and expanding T-cells ex vivo that are specific for the antigen presented by the antigen-presenting cells they were contacted with. Optionally, the method comprises the following additional step
d) administration of these in vitro stimulated and expanded antigen-specific T cells to the patient is a setting of adoptive T cell transfer.

The invention further provides for methods of using the modified antigen presenting cells of the invention for treating cancer or infectious diseases such as viral, bacterial or fungal infections e.g. HIV and hepatitis. In case of active immunotherapy for cancer or infectious diseases, the treatment with antigen presenting cells of the invention can be combined or followed by a non-specific treatment of immunomodulation in order to boost the immune system of the patient. In case of cancer treatment, this can be an anti-CTLA4 antibodies or IFN-alpha or other methods of immunomodulation in order to boost the immune system of the patient.

Providing the antigen presenting cells such as dendritic cells (DCs), B-cells, dendritic cell-lines, or B-cell-lines with a maturation signal through mRNA electroporation offers several advantages:

First there is no need to preincubate the antigen presenting cells for up to 48 hours with soluble maturation signals like pro-inflammatory cytokines or TLR ligands to achieve activation of the antigen presenting cell, which can render the cells "exhausted" and inferior for vaccination purposes. As a result, antigen presenting cells electroporated with mRNA or DNA encoding two or more immunostimulatory factors (e.g. the TriMix of CD40L, CD70 and caTRLA4), which can be injected into the patient within a few hours after electroporation, will mature and secrete most of their immunostimulatory cytokines and chemokines in situ.

Second, it has been postulated that maturation of antigen presenting cells in situ resembles more closely the physiological process involved in response to pathogen infection, and therefore that in situ maturation may lead to enhanced T cell immunity. Pulsing said antigen presenting cells with a target-specific peptide results in presentation of said peptide to the immune system of the patient.

Further, the inventors show that antigen presenting cells electroporated with mRNA or DNA encoding two or more immunostimulatory factors (e.g. the TriMix of CD40L, CD70 and caTRLA4), can be co-electroporated with antigen-encoding mRNA instead of being pulsed with antigenic peptides. This approach offers several further advantages:

First, the maturation and antigen-loading of the antigen presenting cells can be combined in one simple step. Obviating the peptide pulsing step in the vaccine production thus results in less manipulation of the cells and in less cell-loss and contamination-risk.

Second, by using full length antigen-encoding mRNA all possible antigenic epitopes of the TAA will be presented instead of some selected epitopes. Consequently, this strategy might induce a broader antigen-specific T cell response and it is not dependent on (the knowledge of) each patient's HLA haplotype or on the prior identification of antigen-derived epitopes.

Third, the antigen-encoding plasmid can be genetically modified by adding an HLA class II targeting sequence. This not only routes the antigen to the HLA class II compartments for processing and presentation of HLA class II restricted antigen-derived peptides, but also enhances processing and presentation in the context of HLA class I molecules.

It was further established, that TriMix antigen presenting cells (i.e. electroporated with mRNA encoding CD40L, CD70 and caTRLA4) can almost equally well stimulate MelanA-specific T cells when co-electroporated with whole MelanA-encoding mRNA than when being pulsed with MelanA-derived peptide. Moreover, TriMix antigen presenting cells can stimulate T cells specific for other antigens with a lower precursor frequency both in vitro and in vivo.

DETAILED DESCRIPTION OF THE INVENTION

Figure 1A:
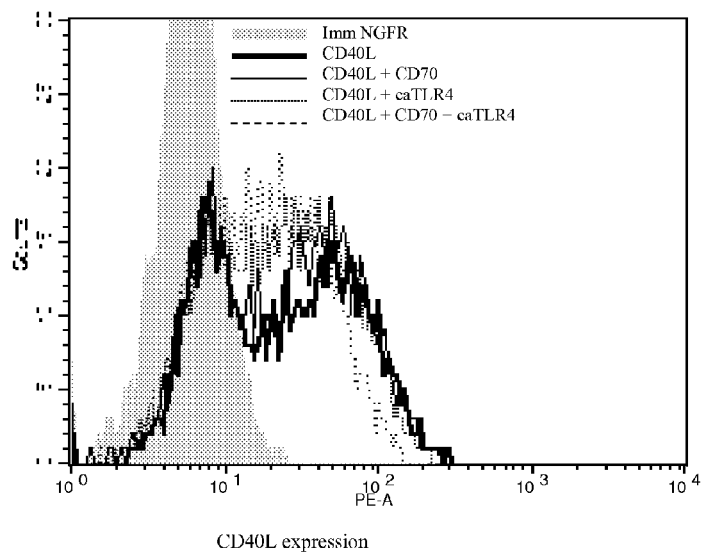
FIG. 1. Transgene expression after mRNA electroporation. (A) DCs were electroporated with CD40L alone or in combination with CD70 and/or caTLR4. Immediately after electroporation, protein transport was blocked with Golgi-plug and after 4 h, cells were stained intracellularly for CD40L. Immature DCs electroporated with irrelevant mRNA were used as negative control. Results are representative for 3 independent experiments. (B) DCs were electroporated with CD70 alone or in combination with CD40L and CD40L together with caTLR4. At several time points after electroporation, DCs were stained for CD70 expression. Immature DCs electroporated with irrelevant mRNA were used as negative control. Results are representative for 3 independent experiments.

In search for new methods for making anti-cancer vaccines, the inventors investigated whether the activation state of DCs is a critical factor in determining whether the DCs presenting a target-specific antigen will be potent inducers of an anti-target immune response after vaccination or not. The inventors unexpectedly found that the effectiveness of currently used DC vaccination protocols could be significantly improved by providing the DCs with a more potent activation signal and by using a shorter manipulation process.

Throughout the invention, the term "TriMix" stands for a mixture of mRNA molecules encoding CD40L, CD70 and caTRLA4 immunostimulatory proteins.

Throughout the invention the term "TriMix DCs" or "TriMix antigen presenting cells" stands for respectively dendritic cells or antigen presenting cells that have been modified to express the TriMix mixture of mRNA molecules encoding CD40L, CD70 and caTLR4 immunostimulatory proteins.

The term "target" used throughout the description is not limited to the specific examples that may be described herein. Any infectious agent such as a virus, a bacterium or a fungus may be targeted. In addition any tumor or cancer cell may be targeted.

The term "target-specific antigen" used throughout the description is not limited to the specific examples that may be described herein. It will be clear to the skilled person that the invention is related to the induction of immunostimulation in antigen presenting cells, regardless of the target-specific antigen that is presented. The antigen that is to be presented will depend on the type of target to which one intends to elicit an immune response in a subject. Typical examples of target-specific antigens are expressed or secreted markers that are specific to tumor, bacterial and fungal cells or to specific viral proteins or viral structures.

Without wanting to limit the scope of protection of the invention, some examples of possible markers are listed below.

The term "antigen presenting cell" used throughout the description includes all antigen presenting cells. Specific non limiting examples are dendritic cells, dendritic cell-lines, b-cells, or B-cell-lines. The dendritic cells or B-cells can be isolated or generated from the blood of a patient or healthy subject. The patient or subject can have been the subject of prior vaccination or not.

The terms "cancer" and/or "tumor" used throughout the description are not intended to be limited to the types of cancer or tumors that may have been exemplified. The term therefore encompasses all proliferative disorders such as neoplasma, dysplasia, premalignant or precancerous lesions, abnormal cell growths, benign tumors, malignant tumors, cancer or metastasis, wherein the cancer is selected from the group of: leukemia, non-small cell lung cancer, small cell lung cancer, CNS cancer, melanoma, ovarian cancer, kidney cancer, prostate cancer, breast cancer, glioma, colon cancer, bladder cancer, sarcoma, pancreatic cancer, colorectal cancer, head and neck cancer, liver cancer, bone cancer, bone marrow cancer, stomach cancer, duodenum cancer, oesophageal cancer, thyroid cancer, hematological cancer, and lymphoma. Specific antigens for cancer can e.g. be MelanA/MART1, Cancer-germline antigens, gp100, Tyrosinase, CEA, PSA, Her-2/neu, survivin, telomerase.

The term "infectious disease" or "infection" used throughout the description is not intended to be limited to the types of infections that may have been exemplified herein. The term therefore encompasses all infectious agents to which vaccination would be beneficial to the subject. Non-limiting examples are the following virus-caused infections or disorders: Acquired Immunodeficiency Syndrome-Adenoviridae Infections-Alphavirus Infections-Arbovirus Infections-Bell Palsy-Borna Disease-Bunyaviridae Infections-Caliciviridae Infections-Chickenpox-Common Cold-Condyloma Acuminata-Coronaviridae Infections-Coxsackievirus Infections-Cytomegalovirus Infections-Dengue-DNA Virus Infections-Contagious Eethyma, -Encephalitis-Encephalitis, Arbovirus-Encephalitis, Herpes Simplex-Epstein-Barr Virus Infections-Erythema Infectiosum-Exanthema Subitum-Fatigue Syndrome, Chronic-Hantavirus Infections-Hemorrhagic Fevers, Viral-Hepatitis, Viral, Human-Herpes Labialis-Herpes Simplex-Herpes Zoster-Herpes Zoster Oticus-Herpesviridae Infections-HIV Infections-Infectious Mononucleosis-Influenza in Birds-Influenza, Human-Lassa Fever-Measles-Meningitis, Viral-Molluscum Contagiosum-Monkeypox-Mumps-Myelitis-Papillomavirus Infections-Paramyxoviridae Infections-Phlebotomus Fever-Poliomyelitis-Polyomavirus Infections-Postpoliomyelitis Syndrome-Rabies-Respiratory Syncytial Virus Infections-Rift Valley Fever-RNA Virus Infections-Rubella-Severe Acute Respiratory Syndrome-Slow Virus Diseases-Smallpox-Subacute Sclerosing Panencephalitis-Tick-Borne Diseases-Tumor Virus Infections-Warts-West Nile Fever-Virus Diseases-Yellow Fever-Zoonoses-Etc. Specific antigens for viruses can be HIV-gag, -tat, -rev or -nef, or Hepatitis C-antigens.

Further non-limiting examples are the following bacteria- or fungus-caused infections or disorders: Abscess-Actinomycosis-Anaplasmosis-Anthrax-Arthritis, Reactive-Aspergillosis-Bacteremia-Bacterial Infections and Mycoses-*Bartonella* Infections-Botulism-Brain Abscess-Brucellosis-*Burkholderia* Infections-*Campylobacter* Infections-Candidiasis-Candidiasis, Vulvovaginal-Cat-Scratch Disease-Cellulitis-Central Nervous System Infections-Chancroid-*Chlamydia* Infections-Chlamydiaceae Infections-Cholera-*Clostridium* Infections-Coccidioidomycosis-Corneal Ulcer-Cross Infection-Cryptococcosis-Dermatomycoses-Diphtheria-Ehrlichiosis-Empyema, Pleural-Endocarditis, Bacterial-Endophthalmitis-Enterocolitis, Pseudomembranous-Erysipelas-*Escherichia coli* Infections-Fasciitis, Necrotizing-Fournier Gangrene-Furunculosis-*Fusobacterium* Infections-Gas Gangrene-Gonorrhea-Gram-Negative Bacterial Infections-Gram-Positive Bacterial Infections-Granuloma Inguinale-Hidradenitis Suppurativa-Histoplasmosis-Hordeolum-Impetigo-*Klebsiella* Infections-Legionellosis-Leprosy-Leptospirosis-*Listeria* Infections-Ludwig's Angina-Lung Abscess-Lyme Disease-Lymphogranuloma Venereum-Maduromycosis-Melioidosis-Meningitis, Bacterial-Mycobacterium Infections-Mycoplasma Infections-Mycoses-*Nocardia* Infections-Onychomycosis-Osteomyelitis-Paronychia-Pelvic Inflammatory Disease-Plague-Pneumococcal Infections-*Pseudomonas* Infections-Psittacosis-Puerperal Infection-Q Fever-Rat-Bite Fever-Relapsing Fever-Respiratory Tract Infections-Retropharyngeal Abscess-Rheumatic Fever-Rhinoscleroma-*Rickettsia* Infections-Rocky Mountain Spotted Fever-*Salmonella* Infections-Scarlet Fever-Scrub Typhus-Sepsis-Sexually Transmitted Diseases, Bacterial-Sexually Transmitted Diseases, Bacterial-Shock, Septic-Skin Diseases, Bacterial-Skin Diseases, Infectious-Staphylococcal Infections-Streptococcal Infections-Syphilis-Syphilis, Congenital-Tetanus-Tick-Borne Diseases-Tinea-Tinea Versicolor-Trachoma-Tuberculosis-Tuberculosis, Spinal-Tularemia-Typhoid Fever-Typhus, Epidemic Louse-Borne-Urinary Tract Infections-Whipple Disease-Whooping Cough-*Vibrio* Infections-Yaws-*Yersinia* Infections-Zoonoses-Zygomycosis-Etc.

The current invention provides new methods of enhancing the immunostimulatory capacities of human DCs through transfection with at least two different mRNA or DNA molecules encoding molecular adjuvants selected from the list of CD40L, CD70, caTLR4, IL-12p70, EL-selectin, CCR7 and/or 4-1BBL; or in combination with the inhibition of the expression or function of SOCS, A20, PD-L1 or STAT3, for example through siRNA transfection.

The use of the combination of CD40L and caTLR4 in monocyte derived immature DCs through mRNA electroporation generates mature, cytokine/chemokine secreting DCs, as has been shown for CD40 and TLR4 ligation through addition of soluble CD40L and LPS.

The introduction of CD70 into the DCs provides a co-stimulatory signal to $CD27^+$ naive T-cells by inhibiting activated T-cell apoptosis and by supporting T-cell proliferation.

As an alternative to caTLR4, other Toll-Like Receptors (TLR) could be used. For each TLR, a constitutive active form is known, and could possibly be introduced into the DCs in order to elicit a host immune response. In our view however, caTLR4 is the most potent activating molecule and is therefore preferred.

Introduction of mRNA encoding an additional cytokine such as IL-12p70 in the DCs could be beneficial to further increase the cytokine excretion of the DCs, subsequently further stimulating the host immune response.

Additional introduction of EL-selectin or CCR7 into the DCs could be beneficial to promote the in vivo migration of the manipulated DCs towards the lymph nodes, the place were the immune response is naturally initiated in the host.

Further co-stimulatory molecules such as 4-1 BBL or a constitutively active form of Akt could also be introduced in the DCs.

In addition, the expression and/or function of inhibitory molecules such as SOCS, A20, PD-L1, STAT3 could be lowered or halted through additional introduction of specific inhibitory molecules such as specific siRNA molecules in the DCs.

Additional in vitro incubation of the DCs with soluble factors such as TLR ligands, IFN-gamma, TNF-alpha, IL-6, PGE2 and/or IL-1 beta could also be utilised for the maturation of the DCs.

The invention preferably uses DCs derived from peripheral blood mononuclear cells (PBMCs) directly isolated from the patient's blood, but alternatives such as DCs differentiated out of CD34-positive cells or commercially available dendritic cell-lines could be used as well.

The method of the invention uses either mRNA electroporation, viral transduction (e.g. through lentivirus, adenovirus, or vaccinia virus), mRNA lipofection or DNA transfection to introduce immunostimulatory molecules and target-specific antigens into the DCs. mRNA electroporation is especially preferred due to its high efficiency and its wide accepted use in clinical settings in contrast to viral transduction. For introduction of the target-specific antigens, pulsing of the cells with the antigen-specific peptides or with protein can be used as an alternative to mRNA electroporation. The introduced mRNA can be a specifically synthesized sequence based on known tumor-specific markers, or can be isolated from (a) tumor cell line(s) or from a tumor-biopsy of the patient.

For the production of the DCs, the invention preferably uses autologous plasma obtained from the patient, but human AB serum, which is commercially available can also be used.

In a preferred embodiment, the invention lies in the simultaneous introduction of CD40L and CD70 into DCs, thereby leading to increased immunostimulatory effects of the DCs. In a further preferred embodiment, the specific combination of CD40L, CD70 and caTLR4 is used to improve the immunostimulatory effects of the DCs. In both of these embodiments, any of the following markers could be introduced simultaneously: IL-12p70, EL-selectin, CCR7, 4-1 BBL for increased expression or SOCS, A20, PD-L1 or STAT3 inhibition. In addition to the molecular adjuvants, a target-specific antigen or its derived epitopes are introduced into the DCs in order to enable them to elicit a T-cell immune response towards the target-specific antigen. Several of the combinations listed above were shown to have unexpectedly high immunostimulatory effects on the DCs.

Several hurdles had to be taken in order to make the method work. First we assessed transgene expression of CD40L after electroporation into K562 cells and DCs. Although CD40L could be readily detected on the membrane of electroporated K562 cells until 24 h after electroporation, we were unable to detect it on the DC membrane. This is probably due to the fact that newly synthesized CD40L protein rapidly encounters CD40 on the DC membrane and is re-internalized, a process that cannot take place in CD40-negative K562 cells. Indeed, when the trans-Golgi trafficking of CD40L was blocked with brefeldin A, we were able to detect CD40L protein intracellularly in the DCs.

Although strong expression of CD70 on mature murine DCs had been reported after CD40 and TLR ligation alone or in combination, very little is known about the expression of CD70 on human DCs. In our hands, immature DCs, cytokine cocktail matured DCs or DCs electroporated with CD40L and/or TLR4 did not express CD70. Even after combined CD40 ligation through 3T6-associated CD40L and TLR ligation through LPS or dsRNA only a minor percentage of DCs showed CD70 expression. Whether this low CD70 expression by human DCs is a general phenomenon or could be related to our DC generation protocol remains to be established.

These experiments clearly show that the mere extrapolation of the mouse immunostimulatory concept to the human situation is in no way straightforward. In contrast, we had to explicitly induce CD70 expression through electroporation of CD70 mRNA in human DCs. Only then we could establish a strong expression that persisted for several days, which should enable the DCs to interact with $CD27^+$ T-cells for a prolonged period of time.

Although we were technically unable to investigate the expression of the caTLR4 protein, the NF-kappaB activation assay indicates that the mRNA electroporation of our caTLR4 plasmid leads to the expression of a functional protein. In parallel we could also show that the CD40L and CD70 plasmids encode functional proteins since CD40L and CD70 electroporated DCs activate the NF-kappaB signaling pathway after CD40 and CD27 ligation, respectively.

In a further experiment, the inventors investigated the effect of CD40L, CD70 and caTLR4 electroporation in different combinations on the DC phenotype, its cytokine/chemokine secretion pattern and its ability to stimulate naive $CD4^+$ T-cells. For all three properties tested, the same conclusions can be drawn:

[1] Both CD40L and caTLR4 electroporation in DCs induced phenotypical maturation, enhanced cytokine/chemokine secretion and these electroporated DCs stimulated naive $CD4^+$ T-cells to become IFN-gamma producing, Th1 type T-cells,

[2] Combination of CD40L with caTLR4 electroporation boosted the effect even further, while

[3] CD70 (co-)electroporation had no effect on phenotype & chemokine/cytokine secretion (which is as expected because the DC don't express the ligand of CD70 (CD27).

On the phenotype level, we observed an enhanced expression of the costimulatory molecules CD40, CD80, CD83, CD86 and of the HLA class I molecules. Of note, CD40 engagement through CD40L electroporation did not impair the upregulation of CD40 expression. On the cytokine secretion level, we found a marked upregulation in the secretion of the Th1 cytokine IL-12p70, several pro-inflammatory cytokines (IL-1 beta, IL-6, TNF-alpha), hematopoietic growth factors (G-CSF, GM-CSF), IFN-gamma, and IL-10. On the chemokine secretion level, enhanced secretion of IL-8 (recruitment of neutrophils), MIP-1 alpha (recruitment of monocytes and T-cells), IP-10 (IFN-gamma inducible 10 kDa protein; recruitment of monocytes and T-cells) and RANTES (recruitment of T-cells, basophils and eosinophils) was observed. MIP-1 alpha, RANTES and IP-10 are all chemotactic for T-cells, but it has been shown that MIP-1 alpha and RANTES are produced by Th1/Th2-promoting DCs, while IP-10 production is restricted to Th1-promoting DCs. CD70 (co-)electroporation does not induce phenotypical changes or enhanced cytokine/chemokine secretion by DCs, because DCs lack expression of its signaling ligand CD27.

The cytokine and chemokine secretion pattern suggests that DCs electroporated with CD40L and/or caTLR4 mRNA would preferentially induce IFN-gamma producing Th1 cells, a finding that was confirmed in the allogeneic stimulation of $CD45RA^+$ $CD4^+$ T-cells. Indeed, T-cells stimulated with DCs electroporated with CD40L and caTLR4, alone or in combination, produced very high amounts of IFN-gamma, but almost no IL-4 and IL-10, secretion of which was not increased in comparison to T-cells stimulated with DCs electroporated with irrelevant mRNA. We did not observe an increased IFN-gamma secretion by $CD4^+$ T-cells stimulated with CD70 (co-)electroporated DCs, demonstrating that DCs expressing human CD70 do not directly instruct for Th1 development and IFN-gamma secretion. Nonetheless, DCs expressing human CD70 might sensitize naive $CD4^+$ T-cells towards Th1 development through the induction of T-bet and IL-12Rbeta2.

In a following experiment, the inventors analyzed whether DCs electroporated with different combinations of CD40L, CD70 and caTLR4 mRNA exerted costimulatory functions in an antigen-specific setting. We could indeed show that MelanA-A2 peptide pulsed DCs expressing CD40L, CD70 and caTLR4 in different combinations induced increased numbers of MelanA-specific $CD8^+$ T-cells, with the combination of all three molecules yielding the best stimulation. DCs electroporated with CD70 alone did not stimulate an increased number of MelanA-specific $CD8^+$ T-cells in comparison to DCs electroporated with NGFR mRNA. In contrast, CD70 co-electroporation with CD40L, together or not with caTLR4, induced an additional increase of MelanA-specific T-cells when compared to DCs electroporated with CD40L together or not with caTLR4. This is probably due to a survival-effect induced by the ligation of CD70 on the DCs with CD27 on the T-cells during stimulation.

After having established that CD40L, caTLR4 and CD70 expression by DCs increases their ability to stimulate MelanA-specific CD8$^+$ T-cells, we investigated the functional and phenotypical properties of the stimulated T-cells. In correlation with the increased number of MelanA-specific CD8$^+$ T-cells, more IFN-gamma/TNF-alpha producing cells were generated and a greater number of CD8$^+$ T-cells with a cytolytic capacity could be detected. When analyzing the phenotype of the MelanA-specific CD8$^+$ T-cells, all cells appeared to be CD45RA$^-$CD45RO$^+$CD27$^+$CD28$^+$, together with a variable expression of CD62L and CCR7. This indicates that central memory T-cells (CD62L$^+$ and CCR$^+$) have been induced as well as early effector memory T-cells or EM$_1$ cells (CD62L$^-$ and CCR7$^-$), depending on the nomenclature.

The results of the experiments listed below in the examples clearly establish a proof-of-principle that DCs co-electroporated with mRNA encoding multiple stimulating proteins and pulsed with antigenic peptide are better T-cell stimulators than immature or cytokine cocktail matured DCs. Moreover, it is possible to co-electropate these DCs with target-specific antigen encoding mRNA, thus providing its full antigenic spectrum. Additional data where DCs were co-electroporated with CD40L, CD70, and caTLR4 mRNA together with mRNA encoding the MelanA antigen linked to the HLA class II targeting signal of DC-LAMP indicate that these cells are also superior in inducing MelanA-specific CD8$^+$ T-cells, leading to a fold increase of 300 in comparison to immature DCs. Data suggest that DCs co-electroporated with CD40L, CD70 and caTLR4 mRNA are also able to prime T cells specific for target-associated antigens other than MelanA, in particular for MAGE-A3, gp100 and tyrosinase; antigens for which lower T cell precursor frequencies have been reported. It is clear that the present invention should not be regarded as being limited to the examples used to proof the concept of using the antigen presenting cells of the invention to create an immune response in a subject. Any possible antigen to which an immune response could be beneficial for a subject can be envisaged and is an integral part of the invention. Markers can be tumor-specific markers or can be virus-specific, bacterium-specific or fungal specific.

The invention provides for the first time evidence that genetically modified DCs expressing at least two stimulating molecules selected from the lot of CD40L, CD70 and caTLR4, IL-12p70, EL-selectin, CCR7, 4-1BBL; or in combination with suppression of SOCS, A20, PD-L1 or STAT3 offer a DC based vaccine possessing all the features considered necessary for induction of optimal target-reactive immune responses. In a preferred embodiment of the invention the combination of stimulating molecules is CD40L and CD70. In a further preferred embodiment, the specific combination of stimulating molecules is the TriMix of CD40L, CD70 and caTLR4.

Of importance is that in the methods of the invention, all antigen-specific stimulations were performed without the addition of any exogenous IL-2 and/or IL-7 to support T-cell proliferation and survival, which is in contrast to most studies reporting in vitro stimulations. In our opinion, omitting exogenous cytokines creates a less artificial environment and is closer to the situation in vivo. Indeed, it has been shown that addition of 50 IU/ml IL-2 during antigen-specific stimulation had no effect on the number of antigen-specific T-cells induced, but did influence the functional profile of the induced specific T-cells, namely by increasing both the number of lytic and of IFN-gamma/TNF-alpha secreting T-cells, indicating that addition of exogenous cytokines to T-cell stimulations can alter the outcome of monitoring techniques.

The use of the methods of the invention has a further advantage over the prior art in that the in vitro manipulation of the DCs is reduced to a minimum in order to prevent the excretion of physiologically relevant cytokines in the in vitro culture medium. This is achieved by using a highly efficient one-step transduction method, preferably through mRNA electroporation, enabling the simultaneous introduction of at least two mRNA molecules encoding molecular adjuvants (possibly in combination with a target-specific antigen). This enables the DCs to release their natural cytokines in their future environment, be it in vitro for the experiments or in vivo in the patient, leading to an increased T-cell immune response.

In an additional embodiment, the DCs of the invention are useful in methods for identifying new target-specific markers. The modified DCs can be used to stimulate T cells from healthy donors or patients having cancer or an infectious disease, who were or were not previously vaccinated with a vaccine containing a target-specific antigen. Subsequently, after one or more stimulations with modified DCs, the target-antigen specific T cells can be identified and the target-antigen derived epitope against which the T cells are responding, can be characterized.

It was first shown that human, monocyte derived DCs electroporated with mRNA encoding CD40L, CD70 and caTLR4 mRNA (thus creating TriMix DCs), acquire a mature phenotype, enhance their cytokine and chemokine secretion and have an increased capacity to skew naive CD4$^+$ to a Th1 response and to induce MelanA-specific CD8$^+$ T cells when pulsed with the immunodominant MelanA-A2 peptide.

Further, the inventors show that TriMix DCs can be co-electroporated with tumorantigen-encoding mRNA instead of being pulsed with antigenic peptides. This approach offers several further advantages. First, the maturation and tumor-antigen-loading of the DCs can be combined in one simple step. Obviating the peptide pulsing step in the vaccine production thus results in less manipulation of the cells and in less cell-loss and contamination-risk. Second, by using full-length tumorantigen-encoding mRNA all possible antigenic epitopes of the tumorantigen will be presented instead of some selected epitopes. Consequently, this strategy might induce a broader tumorantigen-specific T cell response and it is not dependent on the knowledge of each patient's HLA haplotype or on the prior identification of tumorantigen-derived epitopes. Third, the tumorantigen-encoding plasmid can be genetically modified by adding an HLA class II targeting sequence. This not only routes the tumorantigen to the HLA class II compartments for processing and presentation of HLA class II restricted tumorantigen-derived peptides, but also enhances processing and presentation in the context of HLA class I molecules.

The inventors confirmed that there were no differences in electroporation efficiency, maturation potential and cytokine secretion when TriMix DCs were prepared as such or co-electroporated with tumorantigen-mRNA.

Further, the inventors showed the capacity of TriMix DCs co-electroporated with tumorantigen mRNA to stimulate both HLA-A2-restricted, MelanA-specific CD8$^+$ T cells and compared it to peptide pulsed TriMix DCs. It was observed that TriMix DCs co-electroporated with sig-MelanA-DCLamp mRNA were indeed able to prime MelanA-specific CD8$^+$ T cells from the blood of healthy donors and that, like their peptide pulsed counterparts, they were much more potent than immature or cytokine cocktail matured DCs.

When compared to peptide pulsed TriMix DCs, the inventors observed that after 1 or 2 stimulations, TriMix DCs co-electroporated with tumorantigen mRNA were slightly less potent than peptide pulsed TriMix DCs, while after 3 stimulations they were equally potent in 2 out of 4 experiments. Although co-electroporated TriMix DCs seem to induce a lower number of epitope specific T cells than their peptide pulsed counterparts in this setting, this does not necessarily mean that they will be less efficient when used for vaccination purposes, and this for a number of reasons. First, when investigating the qualitative functionality of the induced T cells, we consistently observed that the T cells stimulated with co-electroporated TriMix DCs induced more cells secreting both IFN-gamma and TNF-alpha. Moreover, the mean fluorescence intensity of the intracellular IFN-gamma staining was increased, indicating that more cytokine per cell had been produced. These data suggest that these T cells are multifunctional, which has been correlated with a better effector function. Second, as discussed before, by electroporating full-length tumorantigen mRNA linked to a HLA class II targeting signal into the DCs all antigenic epitopes are introduced, including unidentified epitopes and epitopes restricted to all possible HLA haplotypes being HLA class I as well as class II. Therefore, this approach is prone to induce a broader TAA-specific T cell response.

The HLA-A2 restricted immunodominant peptide of MelanA is an epitope for which a very high precursor frequency in the blood exists. We next evaluated whether TriMix DCs co-electroporated with other tumorantigens would be able to induce antigen specific $CD8^+$ T cell responses. Since this work is part of the preclinical assessment of a vaccination study where TriMix DCs co-electroporated with Mage-A3, Mage-C2, Tyrosinase or gp100 mRNA will be injected into melanoma patients, we investigated whether responses specific for these antigens could be induced both in vitro in the blood of unvaccinated melanoma patients and in vivo after vaccination. We observed that in unvaccinated patients, TriMix DCs could indeed stimulate TAA-specific T cells and like for the MelanA antigen, they were more potent than cytokine cocktail matured DCs. Nevertheless, we could only observe specific responses for the HLA-A2 restricted Tyrosinase epitope, as demonstrated by tetramer staining. No responses were observed for the other HLA-A2 restricted Mage-A3, Mage-C2 or gp100 epitopes tested. Moreover, the functional assays did not show that the TriMix DCs had induced T cells specific for other epitopes than the ones tested in tetramer staining, although in these experiments positive results might have been concealed by the relatively high aspecific T cell activation induced by TriMix DCs. This aspecific T cell activation seems inherent to TriMix DCs and occurs both in vitro and in vivo. The reason for this observation remains unclear at this point. On the one hand, it might be due to the fact that DCs electroporated with CD40L and caTLR4 secrete quite high amounts of cytokines and chemokines, which might attract and activate T cells in an aspecific manner. On the other hand, it has been shown that chronic stimulation of naive T cells by antigen-presenting cells continuously expressing CD70, leads to activation of the T cell pool and conversion into effector-memory cells. In this CD70 transgenic mouse model, the T cell activation eventually led to exhaustion of the naive T cell pool and lethal immunodeficiency. Although we also use antigen-presenting cells continuously expressing CD70, we do not expect this in our vaccination study because the T cell pool is not continuously stimulated with CD70, since the DCs are injected bi-weekly and have a limited lifespan in vivo.

When compared to the massive induction of MelanA specific T cells by TriMix DCs, the induction of T cells specific for other target-specific antigens in vitro is rather poor. This is most probably due to the low precursor frequency of the latter. Overall, reports on the induction of Mage-A3, Mage-C3, Tyrosinase or gp100 specific $CD8^+$ T cells by DCs are scarce and comparisons with our results are difficult to make because exogenous IL-2 and/or IL-7 are commonly added during these stimulations, which support T cell activation and proliferation and thus create an artificial T cell stimulatory environment.

Although the responses induced in $CD8^+$ T cells of unvaccinated patients were quite poor, we observed that TriMix DCs are able to induce robust responses for the Mage-A3, Mage-C2 and Tyrosinase antigens through vaccination. Tetramer staining showed that these responses were not directed towards the known HLA-A2 restricted epitopes tested, evidencing the advantage of using full-length tumorantigen mRNA.

Although it is clear that TriMix DCs preferably induce Th1 $CD4^+$ T cells, we had not investigated whether they were also able to process and present HLA class II restricted peptides from electroporated target-specific antigen encoding mRNA. The invention further shows that TriMix DCs co-electroporated with Mage-A3 linked to a HLA class II targeting sequence can indeed stimulate established HLA-DP4 restricted Mage-A3 specific $CD4^+$ T cells. Moreover, their capacity to do so is similar to the $CD4^+$ T cell stimulatory capacity of peptide pulsed cells.

The invention therefore clearly provides the proof of concept that TriMix DCs pulsed with a target-specific peptide or co-electroporated with mRNA encoding a target-specific antigen can stimulate antigen-specific T cells both in vitro and after vaccination and thus form a promising new approach for anti-tumor, anti-viral, anti-bacterial or anti-fungal immunotherapy.

The ultimate goal of the invention is to provide an anti-target vaccine that is capable of eliciting or enhancing a host-specific immune response in either a cancer patient or in a patient infected with a virus, bacteria or fungus. To this end, the DCs are modified with at least two immunostimulatory molecules and a target-specific antigen or target-antigen derived epitope(s) in vitro and reintroduced into the patient intradermally. In the patient, the DCs are able to stimulate T-cells and elicit a host-mediated immune response due to their specific immunostimulatory characteristics. The immune reaction in the host can then be analyzed through known techniques. Analyzing the increase of inflammatory markers point to the establishment of an immune reaction in the host, probably directed towards the target antigen. In order to check whether the immune response is specifically directed towards the target antigen presented by the DCs in the vaccine preparation, several known techniques such as intracellular cytokine staining through flow cytometry, ELISPOT or Enzyme Linked Immuno-Sorbent Assays (ELISA) using peptide fragments of the target antigen or the whole antigen in order to capture and detect antigen specific host T cells can be used. The immune response can be monitored both in the peripheral blood of the patient or in the skin, after the induction of a delayed type hypersensitivity (DTH)-reaction and subsequent biopsy of the DTH region."

The invention further encompasses a method of following the effects of the treatment with an anti-cancer vaccine in a cancer patient, comprising the detection and analysis of the immune response towards the tumor-specific antigen elicited in the subject previously injected with the anti-cancer vaccine obtainable or obtained by the methods of the invention.

In addition, the invention further encompasses a method of following the effects of the treatment with an anti-viral, anti-bacterial or anti-fungal vaccine in a patient respectively infected or at risk of being infected with a virus, bacteria or fungus, comprising the detection and analysis of the immune response towards the target-specific antigen elicited in the subject previously injected with the vaccine obtainable or obtained by the methods of the invention.

The invention further provides a kit for improving the immunostimulatory characteristics of antigen presenting cells comprising a combination of at least two different mRNA or DNA molecules encoding functional immunostimulatory proteins selected from the group consisting of CD40L, CD70, caTLR4, IL-12p70, EL-selectin, CCR7, and/or 4-1BBL; or in combination with molecules inhibiting SOCS, A20, PD-L1 or STAT3 expression or function. In a preferred embodiment, the combination comprises mRNA encoding CD40L and CD70. In a most preferred embodiment, the kit comprises the mRNA coding for the CD40L, CD70 and caTLR4 immunostimulatory molecules.

In a further embodiment, the two or more mRNA or DNA molecules encoding the immunostimulatory proteins are part of a single mRNA or DNA molecule. This single mRNA or DNA molecule is preferably capable of expressing the two or more proteins independently. In a preferred embodiment, the two or more mRNA or DNA molecules encoding the immunostimulatory proteins are linked in the single mRNA or DNA molecule by an internal ribosomal entry site (IRES), enabling separate translation of each of the two or more mRNA sequences into an amino acid sequence. Alternatively, a selfcleaving 2a peptide-encoding sequence is incorporated between the coding sequences of the different immunostimulatory factors. This way, two or more factors can be encoded by one single mRNA or DNA molecule. Preliminary data where cells were electroporated with mRNA encoding CD40L and CD70 linked by an IRES sequence or a self cleaving 2a peptide shows that this approach is indeed feasible.

The invention thus further provides for an mRNA molecule encoding two or more immunostimulatory factors, wherein the two or more immunostimulatory factors are either translated separately from the single mRNA molecule through the use of an IRES between the two or more coding sequences. Alternatively, the invention provides an mRNA molecule encoding two or more immunostimulatory factors separated by a selfcleaving 2a peptide-encoding sequence, enabling the cleavage of the two protein sequences after translation.

In addition, the invention provides an ex vivo method for amplifying antigen-specific T-cells from a patient. This patient could be previously vaccinated or not. This ex vivo amplified pool of T-cells can then be used for the purpose of "adoptive cellular transfer". The adoptive cellular transfer of autologous immune cells that were amplified ex vivo with the aid of the invention could be performed in patients that did or did not undergo a conditioning treatment (such as but not restricted to non-myeloablative chemotherapy) and could be performed with or without concomitant administrations of the invention or with or without additional immunomodulatory treatments (such as but not restricted to the administration of cytokines or co-stimulatory signal modifying molecules). The invention thus provides a method for the ex-vivo amplification of a pool of autologous immune cells from a patient comprising;
a) obtaining or providing T-cells from a patient which was vaccinated prior to the isolation or not,
b) bringing the T-cells ex vivo into contact with antigen-presenting cells or immunotherapy agent obtained by the method according to the invention,
c) identifying, isolating and expanding T-cells ex vivo that are specific for the antigen presented by the antigen-presenting cells they were contacted with (these antigens could either be defined or undefined as would be the case if total tumor RNA would be used as a source of antigen).
d) administration of these in vitro stimulated and expanded antigen-specific T cells to the patient is a setting of an adoptive T cell transfer treatment protocol involving either or not preconditioning regimens and concomitant immunomodulatory treatment.

The invention further provides for methods of treating a patient in need thereof with a pool of antigen presenting cells of the invention or with the vaccine of the invention.

The invention further provides for methods of using the modified antigen presenting cells of the invention for treating cancer or infectious diseases (such as viral, bacterial or fungal infections e.g. HIV and hepatitis virus infections). In case of active immunotherapy for cancer or infectious diseases, the treatment with antigen presenting cells of the invention can be preceded by, combined with or followed by any non-specific treatment of immunomodulation in order to improve the activity of the invention itself or to exploit any synergy between the different treatment modalities (e.g. by improving the immune response to the invention through non-specific stimulation of the patient's immune system with cytokines (e.g. interleukin-2 or Interferon alfa-2b) or TLR-ligands; or e.g. by combination of the invention with a co-stimulatory signal modifying drug such as ipilimumab or tremelimumab); or any other form of immunotherapy. The invention also provides for complex treatment regimens in which the invention itself and a defined number of other immunomodulatory treatments are used to result in a more active treatment plan (e.g. the sequential use of the invention with modality 1 (e.g. a cytokine) followed by the use of the invention for ex vivo expansion of vaccinal immune cells followed by an adoptive cellular transfer of these cells followed by a combination treatment of the invention with an additional modality (e.g. a costimulatory receptor signal modifier) or any possible combination of concomitant and/or sequential use of the invention and additional immunomodulatory treatments.

EXAMPLES

The invention is illustrated by the following non-limiting examples

Example 1

Generating Immature Dendritic Cells from Patient Blood Mononuclear Cells (PBMCs)

Day 0: In vitro manipulation of PBMCs: after the patient underwent a leukapheresis in order to obtain a significant number of PBMCs, the leukapheresis product is thoroughly washed and subsequently seeded into cultivation chambers to allow them to adhere to the plastic of the chambers for two hours at 37° C., in the appropriate medium, such as X-VIVO medium, supplemented with 1% autologous plasma, previously obtained from the same patient. After these two hours, the cultivation chambers are washed with e.g. phosphate saline buffer (PBS) in order to remove the non-adherent cells. The adherent cells in turn are further cultivated in culture medium comprising dendritic cell differentiation factors such as GM-CSF (in a concentration of about 1000 U/ml) and IL-4 (in a concentration of 500 U/ml) in an appropriate medium (e.g. RPMI1640) supplemented with 1% autologous patient plasma.

Day 2 and 4: On days 2 and 4, the medium is again supplemented with GM/CSF and IL-4, in the same amounts as on day 0.

Day 6: Immature dendritic cells are harvested from the cultivation chambers and can either be cryopreserved for future use or utilized immediately.

Cryopreservation is done in an appropriate medium such as 1 ml autologous patient plasma complemented with 10% DMSO and 2% glucose. Between 5 and 20 $10^6$ dendritic cells are frozen per container and freezing is performed according to standard techniques in liquid nitrogen at −192° C.

Example 2

Modifying the Obtained Dendritic Cells Such that they Express Both a Tumorantigen Derived Peptide and the CD40L, CD70 and TLR4 Immunostimulatory Factors to Obtain an Anti-Tumor Vaccine Materials and Methods:
Genetic Constructs.

The cloning of the pGEM4Z-NGFR plasmid encoding a truncated form of the nerve growth factor receptor (extracellular and transmembrane fragment) has previously been described. CD40L was amplified from activated CD4$^+$ T cell cDNA with the following primers: CD40LS 5'-GATGGATC-CGTCATGATCGAAACATACAAC-3' (SEQ ID NO:3) and CD40LAS 5'-GCT CGGTACCCATCAGAGTTTGAG-TAAGCC-3' (SEQ ID NO:4) and was inserted in the pGEM4Z-A64 plasmid (kindly provided by Dr. N. Schaft, Department of Dermatology, University Hospital of Erlangen, Germany) as a BamHI-KpnI fragment. CD70 was amplified from the pIRESneo2-CD70 plasmid (a kind gift from Dr. S. Iwamoto, Department of Biochemistry, Showa University, Japan) with the following primers: CD70S 5'-AAAAGCT-TCCACCATGCCGGAGGAGGGTTC-3' (SEQ ID NO:5) and CD70AS 5'-GGGGGGAATTCTCAGGGGCGCAC-CCAC-3' (SEQ ID NO:6) and was inserted in the pGEM4Z-A64 plasmid as a HindIII-EcoRI fragment. For the cloning of the pGEM4Z-caTLR4-A64 plasmid, the leader sequence (sig) of LAMP1 was fused to human TLR4, truncated between aa M620 and P621, thus deleting the extracellular, LPS-binding domain and creating the constitutively active form of TLR4. caTLR4 was amplified from human mature DC cDNA with the following primers: caTLR4S 5'-GGG-GATCCTGTGCTGAGTTTGAATA TCACC-3' (SEQ ID NO:7) and caTLR4AS 5'-GGGAATTCTCAGATAGATGT-TCTTCCTG-3' (SEQ ID NO:8). caTLR4 cDNA was inserted into the pGEM4Z-sig-LAMP1-A64 as a BamHI-EcoRI fragment, hereby deleting the LAMP1 targeting sequence from the vector. In parallel the caTLR4 cDNA was also inserted as a BamHI-EcoRI fragment into the pcDNA3 vector containing sig.

In vitro transcription of capped mRNA and mRNA electroporation of DCs. Capped mRNA encoding the different immunostimulatory molecules was transcribed from linearized plasmid DNA with T7 polymerase. On day 6, $4\times10^6$ DCs obtained as in example 1 were electroporated with 10 µg of each mRNA. Electroporation was performed in 200 µl Optimix solution B (Equibio) in a 4 mm electroporation cuvette, using the EQUIBIO Easyject Plus® apparatus. The following conditions were used for electroporation: voltage 300 V, capacitance 150 µF and resistance 99Ω, resulting in a pulse time of about 5 ms. Immediately after electroporation, cells were transferred into IMDM containing 1% heat inactivated AB serum (PAA Laboratories, Linz, Austria), PSG, 0.24 mM L-asparagine and 0.55 mM L-arginine (both from Cambrex) (referred to as stimulation medium) at a concentration of $1\times10^6$ cells/ml for further use. No GM-CSF, IL-4 or maturation cytokines were added to the DCs after electroporation.

Synthetic Peptides and Peptide Pulsing.

The HLA-A*0201 restricted MelanA/MART-1 derived peptide corresponding to the optimized immunodominant epitope (aa 26-35; ELAGIGILTV) was purchased from Thermo Electron (Thermo Electron Corporation, Ulm, Germany). The HLA-A2 restricted gag peptide (gag-A2 peptide, HXB2 gag peptidecomplete Set, NIH, AIDS Research & Reference Reagent Program, McKesson BioServices Corporation, Rockville, Md.) was used as a negative control. For peptide pulsing, DC were diluted to a final density of $2\times10^6$ cells/ml in IMDM containing 10 µg/ml peptide and were incubated for 2 h at 37° C.

Flow Cytometry.

Cells were stained using monoclonal antibodies (mAbs) against CD40L-PE or CD70-PE (Beckton Dickinson, BD, San Jose, Calif.). For CD40L staining, DCs were incubated with Golgi-plug (brefeldin A, BD, San Jose, Calif.) for 4 h, after which an intracellular staining for CD40L was performed using the BD Cytofix/Cytoperm plus kit.

Results:
Transgene Expression after mRNA Electroporation.

When K562 cells were electroporated with CD40L mRNA, over 80% of the cells displayed a strong surface expression of CD40L after 4 h. After 24 h, more than 40% of the cells still expressed CD40L (data not shown). In contrast, when DCs were electroporated with CD40L mRNA, no membrane expression could be detected. CD40L could be detected intracellularly, but only when Golgi-plug was added immediately after electroporation to prevent trafficking to the cell membrane. Under these conditions, about 60% of the electroporated DCs expressed CD40L during the first 4 h after electroporation (FIG. 1A). The percentage of positive cells slightly decreased when CD40L mRNA was electroporated in combination with one or two other mRNAs.

Figure 1B:
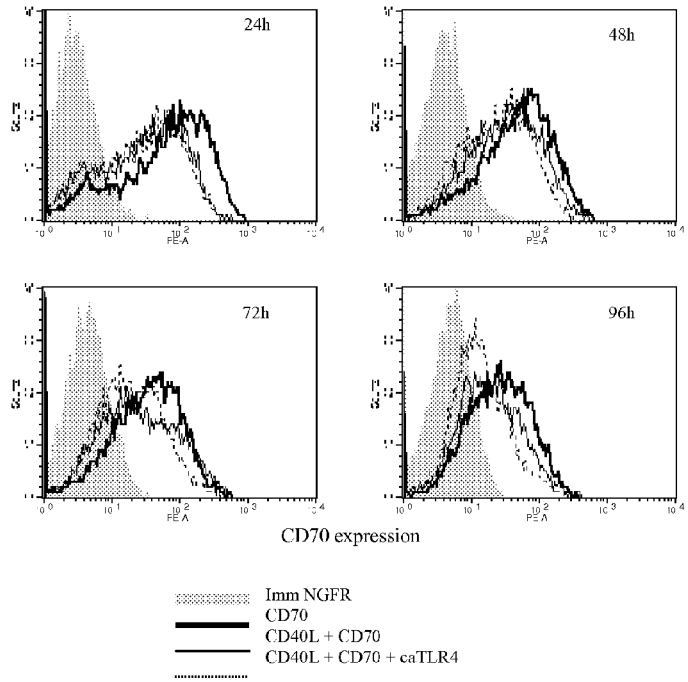

Immature or cytokine cocktail matured DCs showed no expression of CD70 as detected by FACS, nor did DCs electroporated with CD40L and/or caTLR4 mRNA. When these cells were plated on CD40L expressing 3T6 fibroblasts for 48 h, we observed a slight upregulation of CD70 expression in about 3±1.8% (n=2) of the immature DCs and 4.9±2.1% (n=2) of the cytokine cocktail matured DCs (data not shown). When the cells were matured with LPS or by passive pulsing or electroporation with the dsRNA analogue Ampligen, CD70 expression could be detected in about 5.8±0.3%, 9±3.3% and 11.2±3% of the DCs, respectively. On the other hand, DCs electroporated with CD70 mRNA showed a strong and long-lasting expression of CD70 on their membrane (FIG. 1B). Twenty-four hours after electroporation 78% of the electroporated DCs expressed CD70, while 96 h after electroporation, 67% still expressed CD70. Again, CD70 expression DCs slightly diminished when a combination of two or three different mRNAs was electroporated in comparison with CD70 mRNA alone.

DCs already express TLR4 and commercially available antibodies against TLR4 recognize the extracellular domain, which was deleted in the caTLR4 construct. Therefore, we were unable to assess the expression of caTLR4 after mRNA electroporation.

Example 3

Testing the Immunostimulatory Effect of the Obtained Anti-Tumor Vaccine In Vitro Materials and Methods:
Activation of the NF-kappaB Pathway.

The genetic constructs used were as follows: the pNFconluc plasmid encoding the firefly luciferase gene driven by a minimal NF-kappaB-responsive promoter was kindly provided by Dr. R. Beyaert (VIB, Ghent University, Belgium). The CSCW-GLuc-YFP plasmid, encoding the humanized secreted Gaussia luciferase fused to yellow fluorescent protein was a kind gift from Dr. B. A. Tannous (Massachusetts General Hospital, Boston, Mass.). The GLuc-YFP was subcloned from this plasmid into the pHR-vector. CD27 was amplified from EBV-B cell cDNA with the following primers: CD27S 5'-AA AAAGCTTCCACCATGGCACGGCCA-CATCCCTG-3' (SEQ ID NO:1) and CD27AS 5'-CCCCTC-GAG TCAGGGGGAGCAGGCAGG-3' (SEQ ID NO:2) and was inserted in the pcDNA3 vector as a HindIII-XhoI fragment.

For NF-kappaB luciferase assay, 293T cells ($1\times10^5$ cells per well) were seeded in 24 well plates. After 24 h, cells were transfected with 10 ng of the pNFconluc reporter gene plasmid, 10 ng pHR-GLuc-YFP and with 100 ng of the pcDNA3-caTLR4 or pcDNA3-CD27 expression plasmid when indicated. Transfections were performed in triplicate with the FuGENE 6 transfection reagent (Roche) and the total amounts of plasmid were kept constant by adding empty pcDNA3 plasmid. Following transfection, $1\times10^5$ electroporated DCs were added to the wells when indicated. Cell extracts were prepared 24 h later, and reporter gene activity was determined by the luciferase assay system (Promega, Leiden, The Netherlands). Results were normalized for the secreted Gaussia luciferase activity.

Flow Cytometry.

DCs were stained using monoclonal antibodies (mAbs) against CD40-PE, CD80-PE, CD83-FITC, CD86-FITC and HLA-ABC-FITC (all from Pharmingen, San Jose, Calif.). T cells were phenotyped with mAbs against CD4-FITC, CD8-FITC, CD8-APC-Cy7, CD27-APC, CD28-APC, CD45RA-biotin, CD45RO-APC, CD62L-FITC (all from Pharmingen) and CCR7-APC (R&D Systems, Oxford, UK). Biotinylated CD45RA was detected with PerCP conjugated streptavidin.

Non-reactive isotype-matched mAbs (Pharmingen) were used as controls. Data were collected using a FACSCanto flow cytometer and analyzed using FACSDiva or CellQuest software. Cells were electronically gated according to light scatter properties in order to exclude dead and contaminating cells.

Cytokine Secretion Assay.

The secretion of 27 different cytokines and chemokines by DCs during the first 24 h after electroporation was assessed with the Bio-Plex human cytokine 27-Plex A panel according to the manufacturer's instructions (Bio-Rad, Nazareth, Belgium).

Induction of a Naive CD4+ T-Cell Response by Electroporated DCs.

Naive CD4+ T-cells were isolated from the non-adherent fraction of peripheral blood mononuclear cells by immunomagnetic selection using the CD4+ T-cell Isolation Kit II (Miltenyi Biotec, Bergisch Gladbach, Germany), after which CD45RA+ T-cells were positively selected using CD45RA microbeads (Miltenyi Biotec). CD4+ T-cells were consistently >85% pure and >90% CD45RA positive (data not shown). Next, $5\times10^4$ naive CD4+ T-cells were co-cultured with $1\times10^4$ allogeneic DCs electroporated with the indicated mRNA. Each coculture was performed in 12-fold in 200 µl stimulation medium per round-bottom 96 well. After 6 days, stimulated T-cells were harvested, resuspended at a density of $1\times10^6$ T-cells/ml stimulation medium in the presence of $4.7\times10^4$ CD3/CD28 T-cell expander beads (Dynal, Invitrogen) and replated at 200 µl per 96-well with round bottom. After 24 h of incubation at 37° C., the supernatant was harvested and assayed for IFN-gamma (BioSource International, Camarillo, Calif.), IL-4 (Pierce Biotechnology, Aalst, Belgium) and IL-10 (R&D Systems) content using commercially available ELISA kits. Each coculture was tested in duplicate in ELISA.

Induction of MelanA-Specific CD8+ T-Cells.

T cells and DCs were obtained from HLA-A2+ healthy donors. DCs were electroporated with the indicated mRNA and immediately pulsed with MelanA-A2 peptide for 2 h. After washing, peptide-pulsed mRNA electroporated DC were co-cultured with $10\times10^6$ autologous CD8+ T-cells purified through immunomagnetic selection by using CD8 microbeads (Miltenyi). CD8+ T-cells were consistently >90% pure (data not shown). Stimulations were carried out at a DC:T cell ratio of 1:10 in 5 ml stimulation medium per 6 well. CD8+ T-cells were restimulated weekly with the same stimulator DCs as used in the primary stimulation. After 3 rounds of stimulation, CD8+ T-cells were harvested and their antigen specificity and function were determined.

Tetramer Staining.

T cells were stained with 10 nM PE-labeled HLA-A2 tetramers containing either MelanA (ELAGIGILTV) or MAGE-A3 (FLWGPRALV) peptides. Tetramers were prepared in-house. Subsequently, cells were stained with a FITC-labeled anti-CD8 Ab and $1\times10^5$ cells were analyzed by flow cytometry.

Intracellular Cytokine Staining.

The ability of MelanA primed CD8+ T-cells to produce cytokines upon specific restimulation was investigated using intracellular staining for IFN-gamma and TNF-alpha according to the manufacturer's instructions. T2 cells pulsed with MelanA-A2 or gag-A2 peptide were co-cultured with primed CD8+ T-cells at a responder:stimulator ratio of 10:1 for 2-3 h at 37° C. Golgi-plug was then added to block cytokine secretion and cells were incubated for an additional 12 h at 37° C. CD8+ T-cells were then stained with APC-Cy7-conjugated anti-CD8, washed, permeabilized and stained intracellularly with IFN-gamma-PE/TNF-alpha-FITC using the BD Cytofix/Cytoperm plus kit. One hundred thousand cells were analyzed by flow cytometry to assess the percentage of cytokine producing CD8+ T-cells.

CD107a Mobilization Assay.

$1\times10^5$ primed CD8+ T-cells were restimulated with $4\times10^4$ MelanA-A2 or gag-A2 peptide loaded T2 cells in the presence of Golgi-stop (monensin, BD) and either PE-Cy5-labelled anti-CD107a mAb or an irrelevant isotype control. After 12 h of incubation at 37° C., cells were harvested, stained with FITC-labeled anti-CD8 mAb and $1\times10^5$ cells were analyzed by flow cytometry to assess the percentage of CD8+CD107a+ T-cells.

Results:
Activation of the NF-kappaB Pathway.

Figure 2:
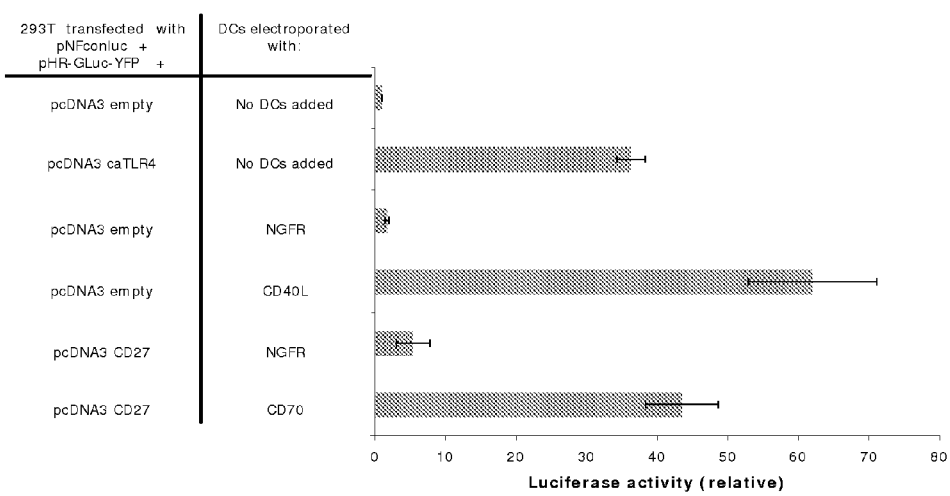
FIG. 2. NF-kappaB activation assay. 293T cells were transfected with the pNFconluc reporter gene plasmid (encoding the firefly luciferase gene driven by a minimal NF-kappaB-responsive promoter) and the pHR-GLuc-YFP plasmid (encoding the humanized secreted Gaussia luciferase fused to yellow fluorescent protein). When indicated, cells were co-transfected with the pcDNA3-caTLR4 or pcDNA3-CD27 expression plasmid. Of note, 293T cells endogenously express CD40. Transfections were performed in triplicate and the total amounts of plasmid were kept constant by adding empty pcDNA3 plasmid. Following transfection, $1\times10^5$ DCs electroporated with CD40L or CD70 mRNA were added when indicated. After 24 h, luciferase activities were determined and normalized on the basis of secreted Gaussia luciferase activity. Results are shown as mean±SD and are representative for 3 independent experiments.

As shown in FIG. 2, when compared to DCs electroporated with NGFR mRNA, both DCs electroporated with CD40L and CD70 mRNA led to NF-kappaB activation in 293T cells expressing CD40 or CD27, respectively. Although this type of experiment was not feasible with caTLR mRNA, we could show that 293T cells co-transfected with caTLR4 DNA (encoding the same protein as the caTLR4 mRNA) and NFkappaB reporter plasmid also led to an activation of the NF-kappaB pathway when compared to 293T cells co-transfected with NF-kappaB reporter plasmid and empty pcDNA3 plasmid (FIG. 2). These data indicate that the CD40L, CD70 and caTLR4 mRNAs encode functionally active proteins.

Phenotype of Differently Electroporated DCs.

Figure 3A:
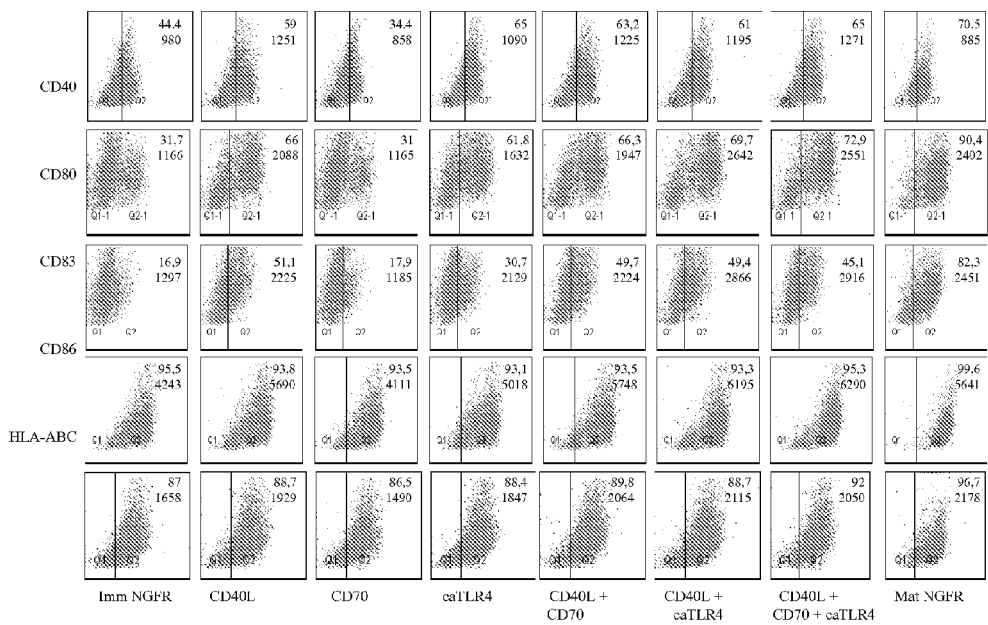
FIG. 3. Electroporating immature DCs with CD40L and/or caTLR4 mRNA induces phenotypic maturation, enhanced IL-12 secretion and stimulation of naive $CD4^+$ T-cells to differentiate into IFN-gamma secreting cells. (A) DCs electroporated with different combinations of CD40L, CD70 and caTLR4 mRNA were stained after 24 h for costimulatory molecules CD40, CD80, CD83 and CD86 and for HLA class I molecules. Percentage of positive cells and mean fluorescence intensity are indicated. Results are representative for at least 8 independent experiments. (B) IL-12p70 produced within 24 h after electroporation was dosed in the supernatant. Each dot represents one individual experiment and the mean is indicated by a horizontal line. (C) Electroporated DCs were used to stimulate allogeneic $CD45RA^+$ naive $CD4^+$ T-cells. Six days later, $CD4^+$ T-cells were restimulated with CD3/CD28 T-cell expander beads. After 24 h, IFN-gamma secretion was assessed in the supernatant by ELISA. Each dot represents one individual experiment and the mean is indicated by a horizontal line.

We assessed the phenotype of DCs electroporated with the different combinations of CD40L, CD70 and caTLR4 mRNA and compared it to immature (1 mm) and cytokine cocktail matured (Mat) DCs electroporated with irrelevant NGFR mRNA as negative and positive controls, respectively. As shown in FIG. 3A, electroporation of immature DCs with CD40L and/or caTLR4 mRNA induced a marked upregulation of the costimulatory molecules CD40, CD80, CD83 and CD86 and of HLA class I molecules. Overall, caTLR4 mRNA electroporated DCs showed a slightly less pronounced phenotypical maturation than CD40L mRNA electroporated DCs whereas the combination of CD40L and caTLR4 mRNA induced the most pronounced phenotypical maturation, which was comparable with the maturation induced by the cytokine cocktail. In contrast, CD70 electroporation or co-electroporation had no effect on the DC's phenotype.

Cytokine/Chemokine Secretion by Differently Electroporated DCs.

Figure 3B:
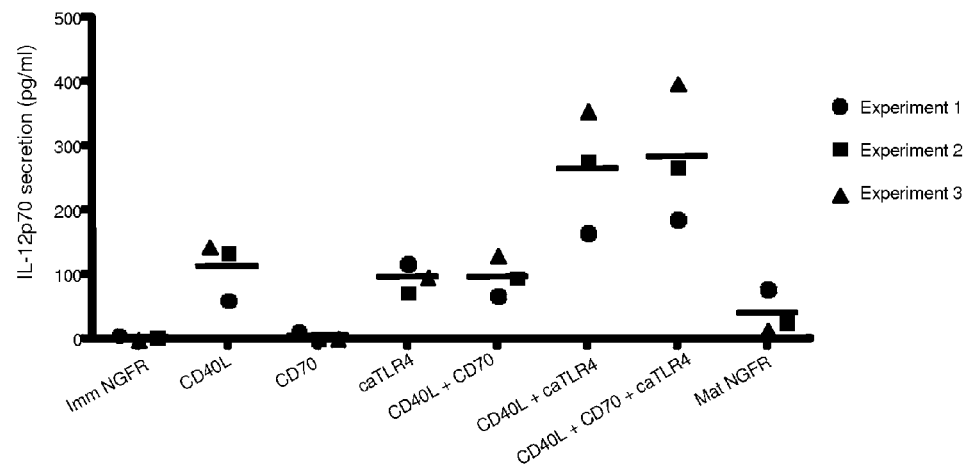

In addition to a phenotypical maturation, electroporation with CD40L or caTLR4 mRNA induced an enhanced secretion of bioactive IL-12p70. Combination of CD40L and caTLR4 boosted the IL-12p70 production even further. Again, CD70 electroporation or co-electroporation had no effect (FIG. 3B). We also investigated the secretion of several other cytokines and chemokines. Secretion by DCs co-electroporated with CD40L, CD70 and caTLR4 mRNA, compared to immature and cytokine cocktail matured DCs electroporated with irrelevant NGFR mRNA is shown in Table 1. For each cytokine/chemokine listed in Table 1, we found that CD70 (co-)electroporation had no effect, whereas CD40L and caTLR4 electroporation increased cytokine/chemokine secretion, and the combination of both yielded the highest secretion. Furthermore, we observed no secretion of IL-2, IL-4, IL-5, IL-7, IL-9, IL-13, IL-15, IL-17, eotaxin, FGF basic or PDGF by any of our DC preparations.

TABLE 1

Cytokine and chemokine production (pg/ml) by electroporated DCs. DCs were electroporated with irrelevant mRNA or the combination of CD40L, CD70 and caTLR4 mRNA. After electroporation, DCs were cultured for 24 h at a cell density of 1 × 10⁶ cells/ml in stimulation medium without addition of supplemental cytokines. Cytokine and chemokine secretion were measured with the Bio-Plex human cytokine 27-Plex A panel. One out of 3 experiments shown.

|  |  | Imm NGFR | CD40L + CD70 + caTLR4 | Mat NGFR |
|---|---|---|---|---|
| Cytokines | IL-1beta | 7.2 | 146 | 3.5 |
|  | IL-6 | 754 | >20000 | 1093 |
|  | IL-10 | 43.4 | 902 | 54.1 |
|  | G-CSF | 140 | 8553 | 68 |
|  | GM-CSF | 9 | 101 | 10.3 |
|  | IFN-gamma | 51.5 | 508 | 71.6 |
|  | TNF-alpha | 87.2 | >20000 | 20 |

TABLE 1-continued

Cytokine and chemokine production (pg/ml) by electroporated DCs. DCs were electroporated with irrelevant mRNA or the combination of CD40L, CD70 and caTLR4 mRNA. After electroporation, DCs were cultured for 24 h at a cell density of 1 × 10⁶ cells/ml in stimulation medium without addition of supplemental cytokines. Cytokine and chemokine secretion were measured with the Bio-Plex human cytokine 27-Plex A panel. One out of 3 experiments shown.

|  |  | Imm NGFR | CD40L + CD70 + caTLR4 | Mat NGFR |
|---|---|---|---|---|
| Chemokines | IL-8 | 10521 | >30000 | 3143 |
|  | MIP-1alpha | 175 | 917 | 120 |
|  | IP-10 | 1076 | >20000 | 50.5 |
|  | RANTES | 1071 | >20000 | 598 |

Stimulation of Naive CD4⁺ T-cells by Differently Electroporated DCs.

Figure 3C:
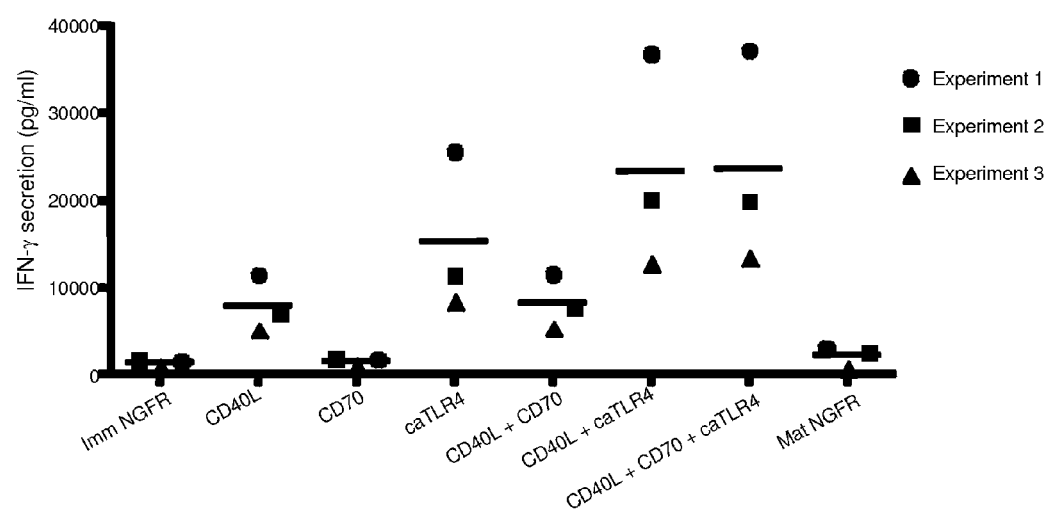

Next, we investigated whether DCs electroporated with different combinations of CD40L, CD70 and caTLR4 mRNA could induce a naive CD4⁺ T-cell response and whether skewing towards a Th1 or Th2 response was observed. Therefore, electroporated DCs were used to stimulate allogeneic CD45RA⁺ CD4⁺ T-cells and after restimulation with CD3/CD28 T-cell expander beads the supernatant was assessed for IL-4, IL-10 and IFN-gamma content. Overall, the stimulated T-cells secreted very low amounts of IL-4 (<50 pg/ml) and IL-10 (<200 pg/ml) and no differences were found between the differently stimulated T-cells (data not shown). On the other hand, DCs electroporated with CD40L and caTLR4 mRNA stimulated the CD4⁺ T-cells to secrete high amounts of IFN-gamma. Here also, combination of CD40L with caTLR4 boosted the IFN-gamma secretion even further and CD70 (co-)electroporation had no effect (FIG. 3C), although FACS analysis confirmed that the CD4⁺CD45RA⁺ T-cells expressed CD27.

Induction of MelanA-Specific CD8⁺ T-Cells by Differently Electroporated DCs.

Figure 4A:
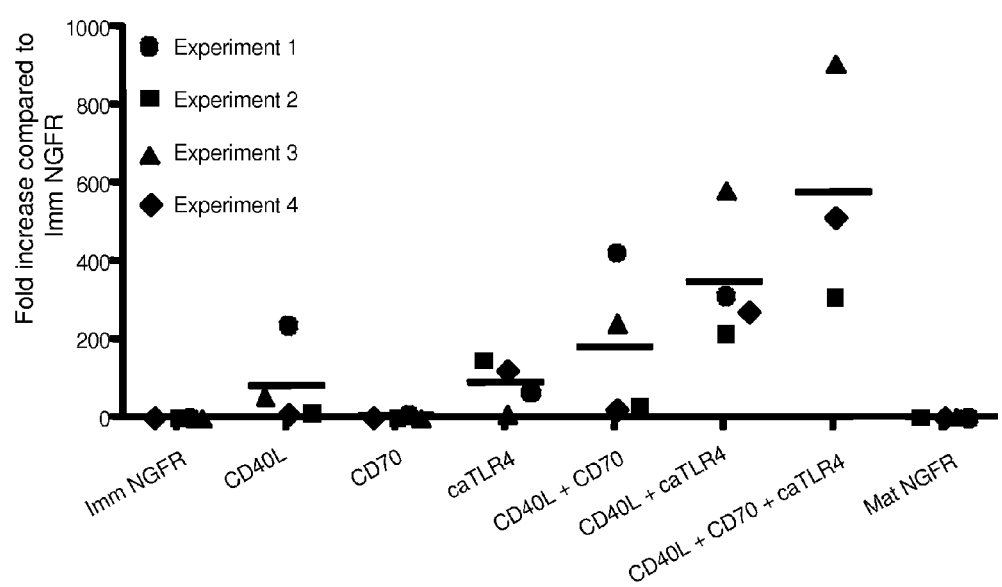
FIG. 4. Increased induction of HLA-A2 restricted MelanA-specific $CD8^+$ T-cells, cytolytic $CD8^+$ T-cells and IFN-gamma/TNF-alpha secreting $CD8^+$ T-cells by DCs electroporated with different combinations of CD40L, CD70 and caTLR4 mRNA and pulsed with MelanA-A2 peptide. (A) Naive $CD8^+$ T-cells were stimulated 3 times with electroporated, peptide pulsed DCs. Then, T-cells were counted and stained for CD8 and MelanA specificity. Fold increase over immature DCs electroporated with irrelevant mRNA is shown. Each dot represents one individual experiment and the mean is indicated by a horizontal line. (B) Cytolytic activity of MelanA-specific T-cells was determined by a CD107a mobilization assay. Primed T-cells were restimulated with T2 cells pulsed with gag or MelanA peptide in the presence of anti-CD107-PE-Cy5 mAb and Golgi-stop. After overnight culture, cells were harvested, stained with anti-CD8-FITC and analyzed by flow cytometry. T-cells were gated on FSC/SSC characteristics and CD8 positivity. (C) Intracellular IFN-gamma/TNF-alpha production by MelanA primed $CD8^+$ T-cells was measured by flow cytometry. Primed T-cells were restimulated with T2 cells pulsed with gag or MelanA peptide in the presence of Golgi-plug. After overnight culture, T-cells were stained for CD8, IFN-gamma and TNF-alpha positivity. T-cells were gated on FSC/SSC characteristics and CD8 positivity. The percentage of IFN-gamma and/or TNF-alpha secreting cells is given, after subtraction of background response induced by T2 pulsed with gag peptide. Results in panels (B) and (C) are given for Experiment 2 (see Table 2). The percentage of MelanA-A2 tetramer positive cells is indicated. For all other experiments, CD107a positivity and IFN-gamma/TNF-alpha secretion correlated with the percentage of MelanA-specific T-cells present in the culture. (D) Phenotype of MelanA-specific $CD8^+$ T-cells. T-cells were stained for CD8 and MelanA-A2 tetramer positivity in combination with the following T-cell markers: CD45RA, CD45RO, CD27, CD28, CCR7 and CD62L. Results are shown for the MelanA-specific $CD8^+$ T-cells induced by DCs electroporated with CD40L, CD70 and caTLR4 mRNA and are representative for all MelanA-specific $CD8^+$ T-cells, irrespective of which DCs were used for stimulation.

In a next set of experiments, we investigated whether DCs electroporated with different combinations of CD40L, CD70 and caTLR4 mRNA could prime naive MelanA-specific CD8⁺ T-cells. Therefore, DCs from HLA-A2⁺ healthy donors were electroporated with different combinations of CD40L, CD70 and caTLR4 mRNA, pulsed with the immunodominant MelanA peptide and co-cultured with autologous CD8⁺ T-cells. Immature and cytokine cocktail matured DCs, electroporated with irrelevant NGFR mRNA and pulsed with MelanA peptide, were used as controls. After 3 weekly stimulations, the number of remaining cells and the percentage of tetramer positive, MelanA-specific CD8⁺ T-cells were determined (Table 2). From these data the absolute number of tetramer positive, MelanA-specific CD8⁺ T-cells (Table 2) and the fold increase over immature DCs electroporated with irrelevant mRNA (FIG. 4A) were calculated. Our data show that electroporating DCs with CD40L or caTLR4 mRNA alone yielded a higher number of MelanA-specific CD8⁺ T-cells, which was further increased by combining CD40L with CD70 or caTLR4 electroporation. Combination of all three molecules consistently resulted in the highest increase of antigen-specific T-cell numbers, with a mean fold increase of 573 and 203 over immature or cytokine cocktail matured DCs electroporated with NGFR mRNA, respectively.

TABLE 2

Induction of HLA-A2 restricted MelanA-specific CD8+ T-cells by DCs electroporated with different combinations of CD40L, CD70 and caTLR4 mRNA and pulsed with MelanA peptide. Results are shown for 4 individual experiments from different healthy donors.

|  | % CD8+ MelanA tetramer+ T-cells/ number of CD8+ T-cells ($10^6$)† | | | | Absolute number of CD8+ MelanA tetramer+ T-cells ($10^3$)‡ | | | |
| --- | --- | --- | --- | --- | --- | --- | --- | --- |
|  | Exp 1 | Exp 2 | Exp 3 | Exp 4 | Exp 1 | Exp 2 | Exp 3 | Exp 4 |
| Imm NGFR | 0.4/3.4 | 0.5/2.1 | 0.1/2.8 | 0.1/1.35 | 13.7 | 10.7 | 2.8 | 1.35 |
| CD40L | 60.2/5.4 | 6.7/2.1 | 5.6/2.8 | 1.1/1.5 | 3271 | 141 | 157 | 16.5 |
| CD70 | 3.3/3.6 | 0.9/1.7 | 0.2/2.2 | 0.2/1.65 | 120 | 15.4 | 4.4 | 3.3 |
| caTLR4 | 20.8/4.3 | 40.3/4.0 | 1.3/2.2 | 9.3/1.8 | 892 | 1596 | 29.1 | 167 |
| CD40L + CD70 | 65/8.9 | 17.3/2.0 | 17.1/4.0 | 1.8/1.75 | 5792 | 348 | 677 | 31.5 |
| CD40L + caTLR4 | 64/6.7 | 49.5/4.7 | 39.9/4.0 | 16.8/2.2 | 4301 | 2317 | 1612 | 370 |
| CD40L + CD70 + caTLR4 | ND/ND | 60.5/5.5 | 40.2/6.2 | 63.2/1.1 | ND | 3303 | 2508 | 695 |
| Mat NGFR | 0.7/3.1 | 1.2/3.4 | 0.4/3.2 | 0.1/1.7 | 21.7 | 41.0 | 12.9 | 1.7 |

†The T-cell population generated after 3 weekly stimulations with electroporated, MelanA peptide pulsed DCs was stained with MelanA loaded HLA-A2 tetramers and anti-CD8 Ab. MelanA-specific CD8+ T-cells were then identified by flow cytometry. Background staining with MAGE-A3-specific HLA-A2 tetramers, which never reached higher than 0.5%, was subtracted. The number of living cells was determined by trypan blue exclusion.
‡Absolute number of MelanA-specific CD8+ T-cells was calculated with the following formula: (number of CD8+ T-cells/100) × % of CD8+ MelanA tetramer+ T-cells.

Functional and Phenotypical Properties of Stimulated CD8+ T-Cells.

Figure 4D:
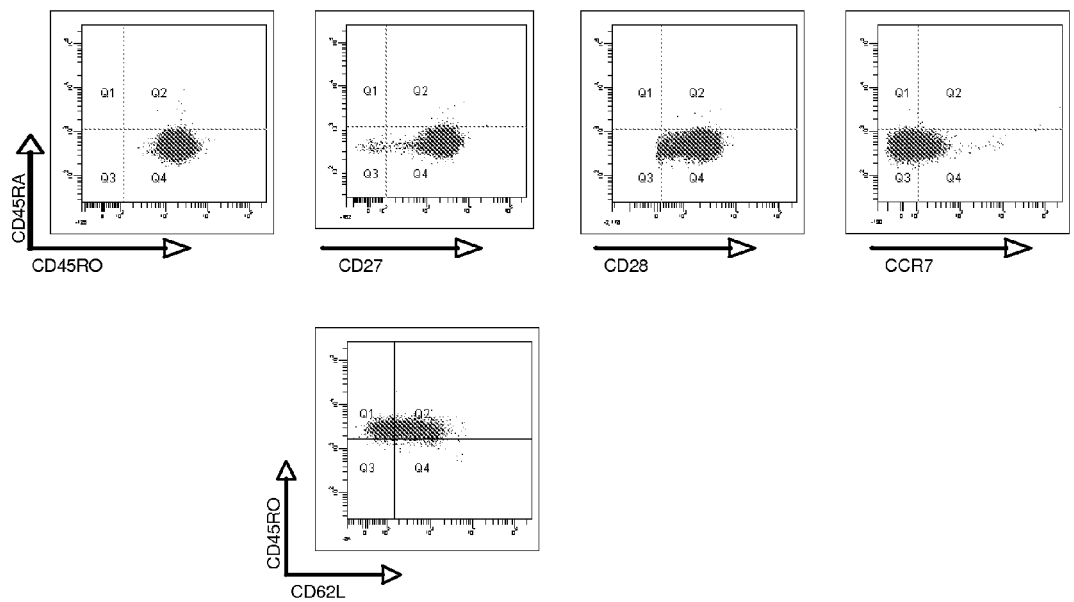

Finally, we assessed the functional and phenotypical properties of CD8+ T-cells stimulated 3 times with differently electroporated, MelanA-A2 peptide pulsed DCs. The main effector mechanisms of stimulated CD8+ T-cells, i.e. cytolysis and cytokine production, were investigated. First we performed a CD107a mobilization assay (FIG. 4B), which measures exposure of CD107a, present on the membrane of cytotoxic granules, onto the T-cell surface as a result of degranulation upon antigenic stimulation. It has been shown that CD107a mobilization can be used as a marker for lytic activity. Second we performed intracellular cytokine stainings to enumerate the number of cells secreting IFN-gamma and/or TNF-alpha, both major mediators of the immune response, upon antigenic stimulation (FIG. 4C). For all donors tested we observed that the percentage of MelanA-specific T-cells, correlated with the percentage of lytic T-cells and with the percentage of IFN-gamma/TNF-alpha producing T-cells. On the other hand, we also analyzed the phenotype of the induced MelanA-specific CD8+ T-cells. The primed CD8+ MelanA-specific T-cells were all CD45RA− CD45RO+CD27+CD28+, together with a variable expression of CD62L and CCR7 (FIG. 4D). Overall, there were no significant differences in the phenotype of the MelanA-specific CD8+ T-cells of the different donors, regardless of which DC type was used for stimulation.

Example 4

TriMix DCs can be Co-Electroporated with TAA mRNA without Affecting Their Electroporation Efficiency, Mature Phenotype and Cytokine Secretion Materials and Methods:
Genetic Constructs.

The pGEM-CD40L, pGEM-CD70, pGEM-caTLR4 plasmids encoding CD40L, CD70 and the constitutively active form of TLR4 (containing the intracellular and transmembrane fragments of TLR4), respectively; the pGEM-NGFR plasmid encoding a truncated form of the nerve growth factor receptor (NGFR, containing the extracellular and transmembrane fragments); and the pGEM-sig-MelanA-DCLamp plasmid encoding the full-length MelanA antigen, containing the optimized immunodominant MelanA-A2 epitope and linked to the DC-Lamp targeting signal have been described. In Vitro Generation of Human Monocyte Derived DCs, In Vitro Transcription of Capped mRNA and mRNA Electroporation of DCs.

Generation, maturation and cryopreservation of immature and cytokine cocktail matured DCs, capped mRNA production and mRNA electroporation of TriMix DCs pulsed with MelanA peptide have been described above. For co-electroporation with tumorantigen mRNA, DCs were electroporated in the same manner as described in example 2, but 20 µg tumorantigen mRNA was included in the mRNA mixture.

Flow Cytometry.

DCs were stained using the following mAbs: CD40-APC, CD70-PE, CD80-PE, CD83-PE, CD86-PE, HLA-ABC-FITC (all from BD Pharmingen, Erembodegem, Belgium) and HLA-DR (purified from clone L243). The anti-HLA-DR antibody was biotin labeled and detected through streptavidin-APC (BD Pharmingen). Non-reactive isotype-matched mAbs (BD Pharmingen) were used as controls. Data were collected using a FACSCanto flow cytometer and analyzed using FACSDiva software. Cells were electronically gated according to light scatter properties in order to exclude dead and contaminating cells.

Cytokine Secretion Assay.

IL-12p70 secretion by DCs during the first 24 h after electroporation was assessed by ELISA using a commercially available kit (eBioscience, Zoersel, Belgium).

Figure 5A:
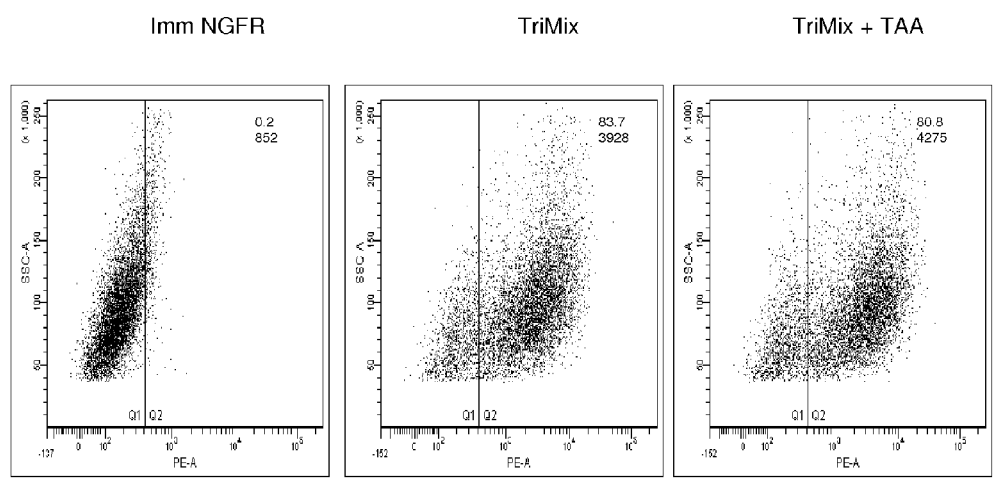
FIG. 5. Electroporation efficiency, phenotype and IL-12p70 secretion by DCs electroporated with TriMix mRNA alone or in combination with tumorantigen mRNA. (A) DCs were electroporated with TriMix (mRNA encoding CD40L, CD70 and caTLR4) mRNA alone or in combination with tumorantigen mRNA. Twenty-four hours later, electroporation efficiency was investigated by staining for surface CD70 expression. Immature DCs electroporated with irrelevant NGFR mRNA were used as negative control. Results are representative for at least 5 independent experiments. (B) Twenty-four hours after electroporation, DCs were stained for costimulatory molecules CD40, CD80, CD83 and CD86 and for HLA class I and II molecules. Percentage of positive cells and mean fluorescence intensity are indicated. Phenotype is compared to immature and cytokine cocktail matured DCs electroporated with irrelevant NGFR mRNA. Results are representative for at least 5 independent experiments. (C) IL-12p70 produced within 24 h after electroporation was dosed in the supernatant. Each dot represents one individual experiment and the mean is indicated by a horizontal line.

Results:

DCs electroporated with a TriMix of CD40L, CD70 and caTLR4 mRNA are typically very efficiently electroporated: on average, about 80% of the DCs express the CD70 molecule on their surface 24 h after electroporation. Because we observed that the electroporation efficiency slightly decreased when a combination of three different mRNAs was electroporated in comparison with a single mRNA, we investigated whether adding a fourth mRNA would affect electroporation efficiency. We found that, when TriMix DCs are co-electroporated with TAA mRNA, electroporation efficiency does not alter notably as demonstrated by CD70 expression 24 h after electroporation (FIG. 5A).

Figure 5B:
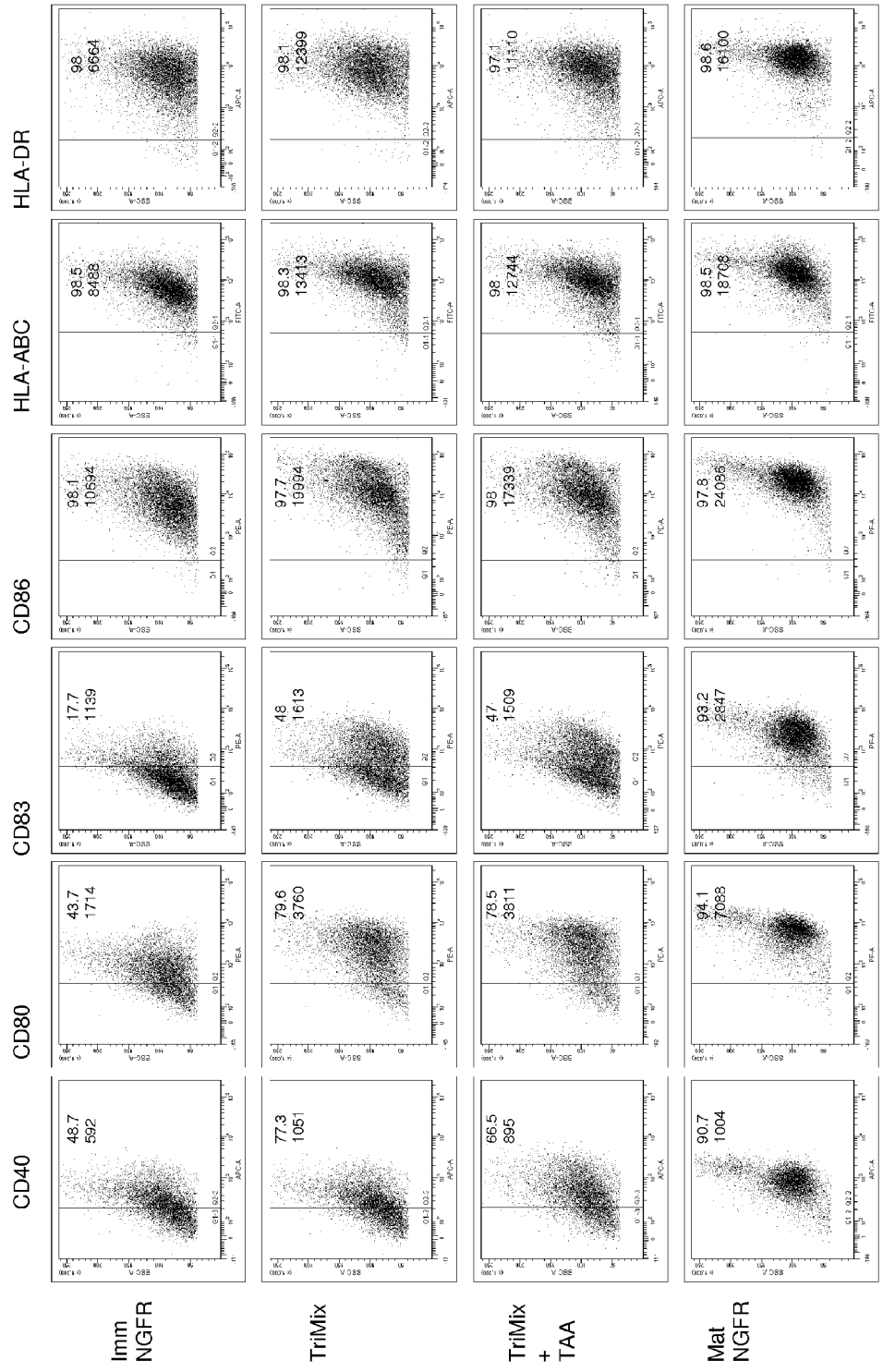
Figure 5C:
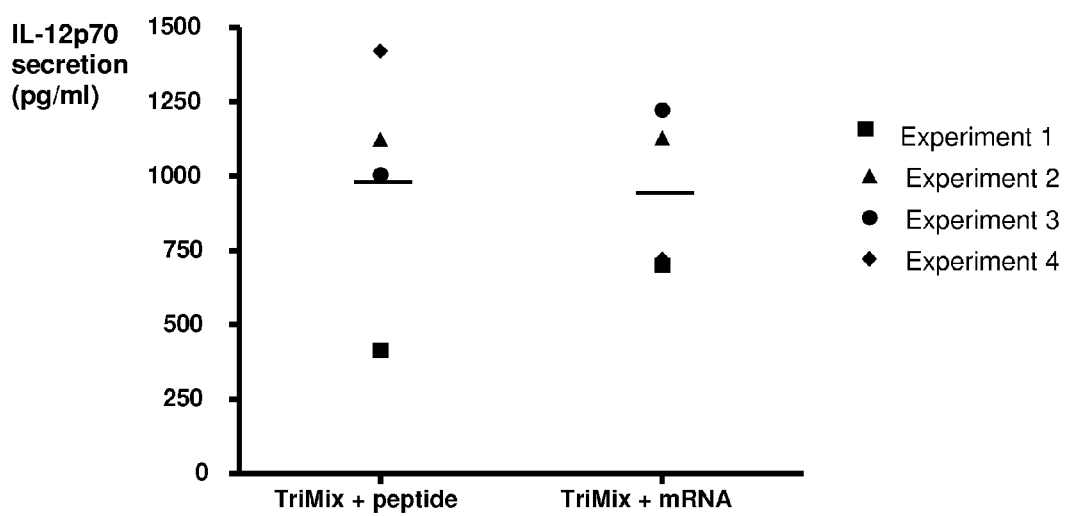

After electroporation with TriMix mRNA, immature DCs acquire a mature phenotype and enhance their cytokine secretion as demonstrated by upregulation of costimulatory molecules (CD40, CD80, CD83, CD86) and HLA-molecules, and IL-12p70 secretion, respectively. Here also, when TriMix DCs are co-electroporated with TAA mRNA the mature phenotype (FIG. 5B) and cytokine secretion (FIG. 5C) are not markedly altered.

Example 5

Induction of MelanA-Specific CD8+ T Cells by TriMix DCs Pulsed with Peptide or Co-Electroporated with Whole Tumorantigen mRNA Materials and Methods:

TriMix DCs pulsed with peptide or co-electroporated with whole tumorantigen mRNA were prepared as described above, as well as the in vitro induction of MelanA specific CD8+ T cells and tetramer staining.

Flow Cytometry.

T cells were phenotyped with the following mAbs: CD8-FITC, CD8-APC-Cy7, CD27-APC, CD28-APC, CD45RA-biotin, CD45RO-APC, CD62L-FITC (all from BD Pharmingen) and CCR7-APC. Biotinylated CD45RA was detected with PerCP conjugated streptavidin (BD Pharmingen). Non-reactive isotype-matched mAbs (BD Pharmingen) were used as controls. Data were collected using a FACSCanto flow cytometer and analyzed using FACSDiva software. Cells were electronically gated according to light scatter properties in order to exclude dead and contaminating cells.

Intracellular Cytokine Staining and CD107a/CD137 Assay.

For intracellular cytokine staining, $2\times10^5$ primed CD8+ T cells were restimulated with $2\times10^4$ stimulator cells in the presence of Golgi-plug (brefeldinA, Becton Dickinson, BD, Erembodegem, Belgium). After 12 h of incubation at 37° C., CD8+ T cells were then stained with FITC or APC-Cy7-conjugated anti-CD8 mAb, washed, permeabilized and stained intracellularly using the BD Cytofix/Cytoperm plus kit with IFN-gamma-PE/TNF-alpha-APC or IFN-gamma-PE/TNF-alfa-FITC, respectively. For the CD107a/CD137 assay, $1\times10^5$ primed CD8+ T cells were restimulated with $2\times10^4$ stimulator cells in the presence of Golgi-stop (monensin, BD) and PE-Cy5-labelled anti-CD107a mAb (BD Pharmingen). After 12 h of incubation at 37° C., cells were harvested and stained with FITC-labeled anti-CD8 mAb and PE-labeled CD137 mAb (both from BD Pharmingen). As stimulator cells, TAP-deficient, HLA-A2+ T2 cells pulsed with peptide or cytokine cocktail matured DCs electroporated with TAA-mRNA were used. Cells were analyzed by flow cytometry using a FACSCanto flow cytometer and FACSDiva software. Cells were electronically gated according to light scatter properties in order to exclude dead and contaminating cells.

Figure 6A:
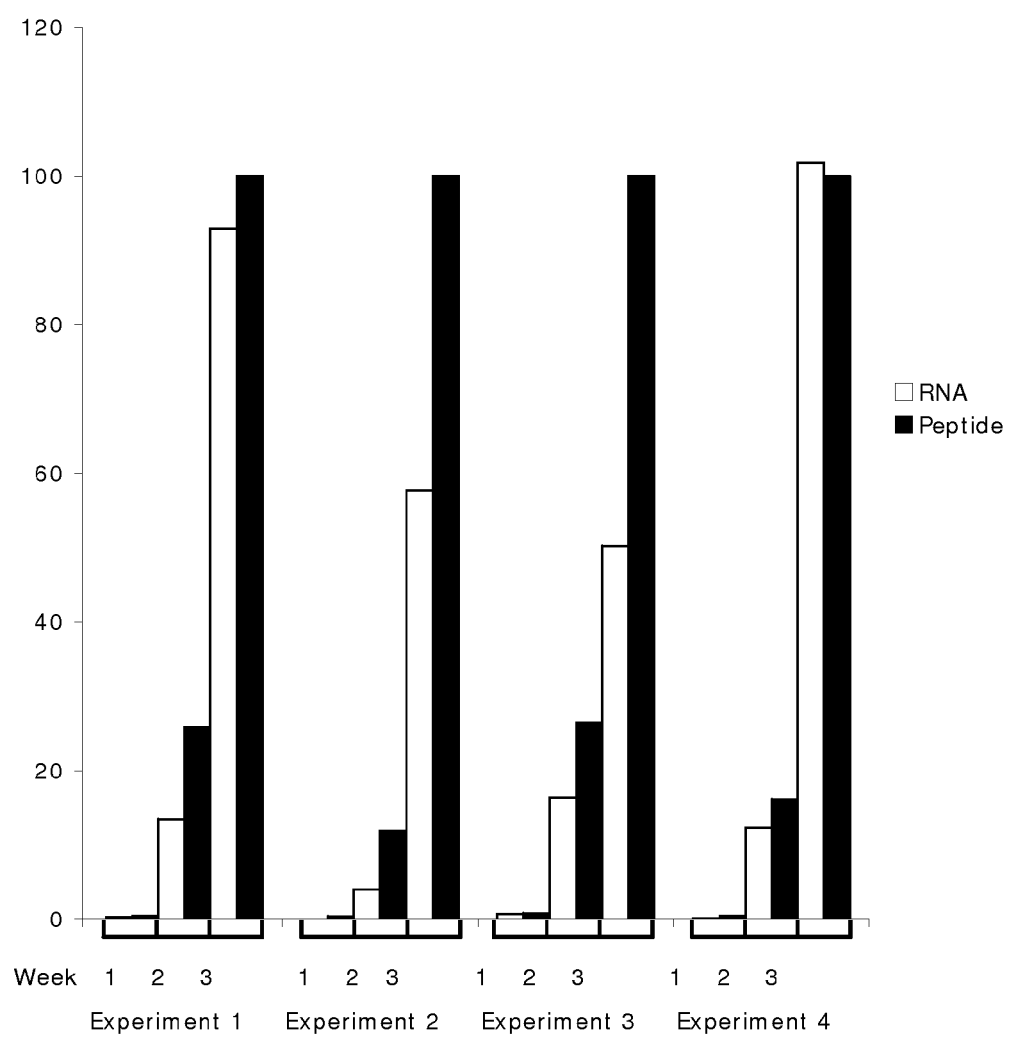
FIG. 6. In vitro induction of HLA-A2 restricted MelanA-specific $CD8^+$ T cells, activated/cytolytic $CD8^+$ T cells and IFN-gamma/TNF-alpha secreting $CD8^+$ T cells by DCs electroporated with TriMix mRNA (mRNA encoding CD40L, CD70 and caTLR4) pulsed with antigenic peptide or co-electroporated with tumorantigen mRNA. (A) Naive $CD8^+$ T cells were stimulated 3 times, with a weekly interval with TriMix DCs, i.e. DCs electroporated with a mixture of mRNA molecules encoding CD40L, CD70 and caTRLA4 immunostimulatory proteins). Every week, T cells were counted, stained for CD8 and MelanA specificity and the absolute number of MelanA-specific $CD8^+$ cells present in the culture was calculated. Relative percentage in comparison with the number of MelanA-specific CD8+ T cells obtained after 3 stimulations with TriMix DCs pulsed with MelanA-A2 peptide (set at 100%) is shown. (B) Activation status and cytolytic activity of MelanA-specific T cells was determined by a CD137/CD107a assay. Primed T cells were restimulated with T2 cells pulsed with gag or MelanA peptide in the presence of anti-CD107-PE-Cy5 mAb and Golgi-stop. After overnight culture, cells were harvested, stained with anti-CD8-FITC, CD137-PE and analyzed by flow cytometry. T cells were gated on FSC/SSC characteristics and CD8 positivity. The percentage of CD137/CD107a double positive cells is given, after subtraction of background response induced by T2 pulsed with gag peptide. (C) Intracellular IFN-gamma/TNF-alpha production by MelanA primed CD8+ T cells was measured by flow cytometry. Primed T cells were restimulated overnight with T2 cells pulsed with gag or MelanA peptide in the presence of Golgi-plug. Then, T cells were stained for CD8, IFN-gamma and TNF-alpha positivity. T cells were gated on FSC/SSC characteristics and CD8 positivity. The percentage of IFN-gamma and/or TNF-alpha secreting cells is given, after subtraction of background response induced by T2 pulsed with gag peptide. Results in panels B and C are given for Experiment 1 (see Table 3). In each experiment, CD137/CD107a positivity and IFN-gamma/TNF-alpha secretion correlated with the percentage of MelanA-specific T cells present in the culture.

Results:

We investigated whether TriMix DCs co-electroporated with full length MelanA-encoding mRNA could prime naive MelanA-specific CD8+ T cells. Therefore, DCs from HLA-A2+ healthy donors were electroporated with TriMix mRNA and either pulsed with the immunodominant MelanA peptide or co-electroporated with MelanA-DCLamp mRNA. The DCs were then cocultured with autologous CD8+ T cells without the addition of exogenous cytokines. Immature and cytokine cocktail matured DCs, electroporated with irrelevant NGFR mRNA and pulsed with MelanA peptide, were used as controls. Cells were stimulated 3 times with a weekly interval. After each stimulation round, the number of remaining cells and the percentage of tetramer positive, MelanA-specific CD8+ T cells were determined and the absolute number of tetramer positive, MelanA-specific CD8+ T cells was calculated (Table 3). Furthermore, the relative percentage of MelanA-specific T cells obtained after each stimulation was compared to the absolute number of MelanA-specific CD8+ T cells obtained after 3 weekly stimulations with peptide-pulsed TriMix DCs (set at 100%) (FIG. 6A). We observed that, after 1 or 2 stimulations, TriMix DCs co-electroporated with TAA mRNA were slightly less potent than peptide pulsed TriMix DCs, while after 3 stimulations, they were equally potent in 2 out of 4 experiments.

Next, we assessed the functional and phenotypical properties of CD8+ T cells stimulated 3 times with TriMix DCs pulsed with peptide or co-electroporated with TAA mRNA. The main effector mechanisms of stimulated CD8+ T cells, i.e. activation, cytolysis and cytokine production, were investigated. T cells were restimulated overnight with T2 cells pulsed with MelanA-A2 peptide or gag peptide as a negative control. First we performed a CD107a mobilization assay combined with a CD137 activation assay (FIG. 6B), which respectively measure lytic activity (14) and T cell activation (15) upon antigenic stimulation. Second we performed intracellular cytokine staining to enumerate the number of cells secreting IFN-gamma and/or TNF-alpha upon antigenic stimulation; both major mediators of the immune response (FIG. 6C). For all donors tested we observed that the percentage of MelanA-specific T cells, correlated with the percentage of lytic/activated T cells and with the percentage of IFN-gamma/TNF-alpha producing T cells. Overall, no major differences were observed between T cells stimulated with peptide pulsed or TAA co-electroporated DCs, except a slight but reproducible increase in mean fluorescence intensity of IFN-gamma staining and also in percentage of IFN-gamma/TNF-alpha double positive cells, suggesting that T cells primed with co-electroporated TriMix DCs exert more functions at once (16). We also analyzed the phenotype of the induced MelanA-specific CD8+ T cells. The primed CD8+ MelanA-specific T cells were all CD45RA−CD45RO+CD27+CD28+, together with a variable expression of CD62L and CCR7 (data not shown), suggesting that both central memory T cells (CD62L+ and CCR7+) and early effector memory T cells (CD62L− and CCR7−) have been induced (17). Overall, there were no significant differences in the phenotype of the MelanA-specific CD8+ T cells of the different donors, regardless of whether peptide pulsed or TAA co-electroporated DCs were used for stimulation.

TABLE 3

Induction of HLA-A2 restricted MelanA-specific CD8+ T cells by TriMix DCs pulsed with MelanA-A2 peptide or co-electroporated with MelanA-DC Lamp mRNA*.

|  | % CD8+ MelanA tetramer+ T cells/ number of CD8+ T cells ($10^6$)† | | | | Absolute number of CD8+ MelanA tetramer+ T cells ($10^3$)‡ | | | |
| --- | --- | --- | --- | --- | --- | --- | --- | --- |
|  | Exp 1 | Exp 2 | Exp 3 | Exp 4 | Exp 1 | Exp 2 | Exp 3 | Exp 4 |
| Imm + MelanA peptide | 0.3/1.2 | 0.1/1.35 | 1.2/4.2 | 0.5/3.5 | 3.5 | 1.3 | 50 | 19 |

TABLE 3-continued

Induction of HLA-A2 restricted MelanA-specific CD8+ T cells by TriMix
DCs pulsed with MelanA-A2 peptide or co-electroporated with MelanA-DC Lamp mRNA*.

| | % CD8+ MelanA tetramer+ T cells/ number of CD8+ T cells (10^6)† | | | | Absolute number of CD8+ MelanA tetramer+ T cells (10^3)‡ | | | |
|---|---|---|---|---|---|---|---|---|
| | Exp 1 | Exp 2 | Exp 3 | Exp 4 | Exp 1 | Exp 2 | Exp 3 | Exp 4 |
| TriMix + MelanA peptide | 72.4/6.8 | 63.2/1.1 | 52.4/9.3 | 49.6/13 | 4922 | 695 | 4884 | 6478 |
| TriMix + MelanA mRNA | 72.5/6.3 | 25.9/1.6 | 43.3/5.7 | 44.8/14.7 | 4572 | 401 | 2455 | 6594 |
| Mat + MelanA peptide | ND | 0.1/1.5 | ND | 2.1/2.4 | ND | 1.5 | ND | 52 |

†The T cell population generated after 3 weekly stimulations with the different DCs was stained with MelanA peptide loaded HLA-A2 tetramers and anti-CD8 Ab. MelanA-specific CD8+ T cells were then identified by flow cytometry. Background staining with MAGE-A3-specific HLA-A2 tetramers was subtracted. The number of living cells was determined by trypan blue exclusion.
‡Absolute number of MelanA-specific CD8+ T cells was calculated with the following formula: (number of CD8+ T cells/100) × % of CD8+ MelanA tetramer+ T cells.
*Results are shown for 4 individual experiments from different healthy donors.

Abbreviations: 1 mm, immature DCs electroporated with irrelevant NGFR mRNA; Mat, cytokine cocktail matured DCs electroporated with NGFR mRNA; ND, not done.

Example 6

Figure 7:
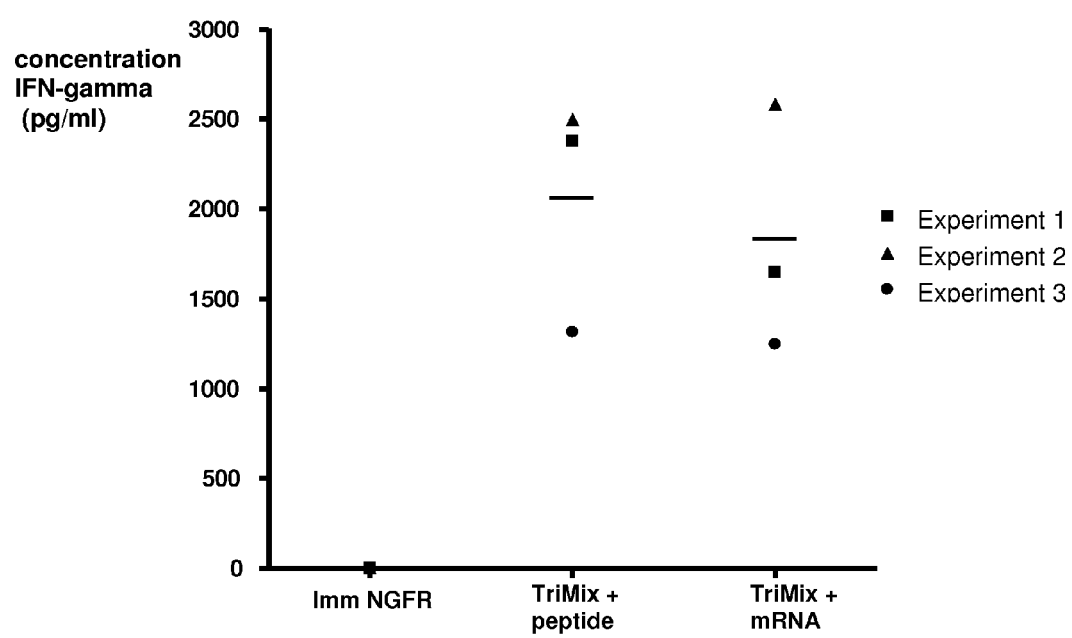
FIG. 7. CD4+ T cell stimulatory capacity of TriMix DCs pulsed with antigenic peptide or co-electroporated with tumorantigen mRNA. DCs were either pulsed with Mage-A3-DP4 peptide or co-electroporated with MageA3-DCLamp mRNA. Four hours later, the cells were cocultured with Mage-A3-specific, HLA-DP4-restricted T cells for 20 h. Immature DCs electroporated with irrelevant NGFR mRNA were used as a negative control. IFN-gamma production is shown. Each dot represents one individual experiment and the mean is indicated by a horizontal line.

Stimulation of Mage-A3-Specific CD4+ T Cells by TriMix DCs Pulsed with Peptide or Co-Electroporated with Whole TAA mRNA Because all TAA-constructs used contain an HLA class II targeting signal, we wanted to investigate whether TriMix DCs co-electroporated with TAA mRNA could stimulate established CD4+ T cells. Therefore, TriMix DCs were either pulsed with Mage-A3-DP4 peptide or co-electroporated with MageA3-DCLamp mRNA. Four hours later, the cells were cocultured with Mage-A3-specific, HLA-DP4-restricted T cells for 20 h. These T cells are HLA-DP4 (HLA-DPB1*0401) restricted and specific for the Mage-A3 epitope aa 243-258 with sequence KKLLTQHFVQENYLEY. Immature DCs electroporated with irrelevant NGFR mRNA were used as a negative control. IFN-gamma released in the supernatant during the coculture was measured by ELISA (FIG. 7). We observed that TriMix DCs are indeed capable of presenting antigenic epitopes in the context of HLA class II molecules, without remarkable differences between peptide pulsed and TAA co-electroporated cells.

Example 7

In Vitro Induction of CD8+ T Cells Specific for Other Antigens than MelanA in the Blood of Unvaccinated Melanoma Patients Materials and Methods:
Genetic Constructs.

The pGEM-sig-MageA3-DCLamp plasmid encoding the full-length Mage-A3 antigen linked to the HLA class II targeting sequence of DC-Lamp (transmembrane/cytoplasmic region) has been described. The pGEM-sig-MageC2-DCLamp plasmid contains the full-length MageC2 gene, flanked by the signal sequence and the HLA class II targeting sequence of DC Lamp. The pGEM-sig-gp100-Lamp and pGEM-sig-Tyrosinase-Lamp plasmids contain the gp100 and Tyrosinase gene respectively, with their own signal sequence and with their transmembrane and cytosolic regions replaced by the HLA class II targeting sequence of Lamp-1.

Electroporation of DCs.

For co-electroporation with MageA3-DCLamp, MageC2-DCLamp, Tyrosinase-Lamp or gp100-Lamp mRNA, 50×10^6 DCs were electroporated with 20 μg of CD40L, CD70 and caTLR4 mRNA together with 60 μg of TAA-encoding mRNA in a 4 mm electroporation cuvette and the following conditions were used for electroporation: voltage 300 V, capacitance 450 pF and resistance 99Ω in a final volume of 600 μl.

Synthetic Peptides and Peptide Pulsing.

The HLA-A*0201 restricted Mage-A3 (aa 112-120; KVAELVHFL), Mage-C2 (aa 336-344; ALKDVEERV), Tyrosinase (aa 369-377; YMDGTMSQV), gp100 (aa 209-217; ITDQVPFSV) and derived peptides were purchased from Thermo Electron (Ulm, Germany). The HLA-A2 restricted gag peptide (gag-A2 peptide, HXB2 gag peptide-complete Set, NIH, AIDS Research & Reference Reagent Program, McKesson BioServices Corporation, Rockville, Md.) was used as a negative control. For peptide pulsing, DC or T2 cells were diluted to a final density of 2×10^6 cells/ml in IMDM containing 10 μg/ml peptide and were incubated for 2 h at 37° C.

Induction of TAA-Specific CD8+ T Cells.

CD8+ T cells were isolated from the blood of HLA-A2+ melanoma patients. CD8+ T cells were purified through immunomagnetic selection by using CD8 microbeads (Miltenyi Biotec, Bergisch Gladbach, Germany) and were consistently >90% pure (data not shown). Twenty million CD8+ T cells were cocultured with autologous DCs at a DC:T cell ratio of 1:10 per 6 well in 7.5 ml stimulation medium consisting of IMDM medium containing 1% heat inactivated AB serum (PAA Laboratories, Linz, Austria), 100 μml penicillin, 100 μg/ml streptomycin, 2 mM L-glutamine, 0.24 mM L-asparagine and 0.55 mM L-arginine (all from Cambrex) without any further addition of exogenous cytokines such as IL-2 or IL-7. As stimulator DCs, DCs matured with the cytokine cocktail containing IL-1 alpha, IL-6, TNF-alpha and PGE$_2$ and pulsed with a HLA-A2-restricted, Mage-A3, Mage-C2, Tyrosinase or gp100 derived peptide (sequences KVAELVHFL, ALKDVEERV, YMDGTMSQV and ITDQVPFSV, respectively; mixed at a 1:1:1:1 ratio); or TriMix DCs as prepared for vaccination were used. CD8+ T cells were restimulated weekly with the same stimulator DCs as used in the primary stimulation. After 2 rounds of stimulation, CD8+ T cells were harvested and their antigen specificity and function were determined.

Tetramer Staining.

T cells were stained with a FITC-labeled anti-CD8 (BD Pharmingen) and with 10 nM PE-labeled HLA-A2 tetramers (prepared in-house). The tetramers contained one of the following HLA-A2 restricted, TAA-derived peptides: FLWGPRALV—SEQ ID NO:9—or KVAELVHFL—SEQ ID NO:10—(Mage-A3-derived); ALKDVEERV—SEQ ID NO:11-(Mage-C2-derived); YMDGTMSQV—SEQ ID NO:12—(Tyrosinase-derived); ITDQVPFSV—SEQ ID NO:13—, YLEPGPVTA—SEQ ID NO:14—or KTWGQYWQV—SEQ ID NO:15—(gp100-derived); or SLLMWITQC—SEQ ID NO:16—(NY-ESO-1-derived, negative control). Cells were analyzed by flow cytometry.

Intracellular cytokine staining and CD107a/CD137 assay were performed as described in example 5.

Figure 8A:
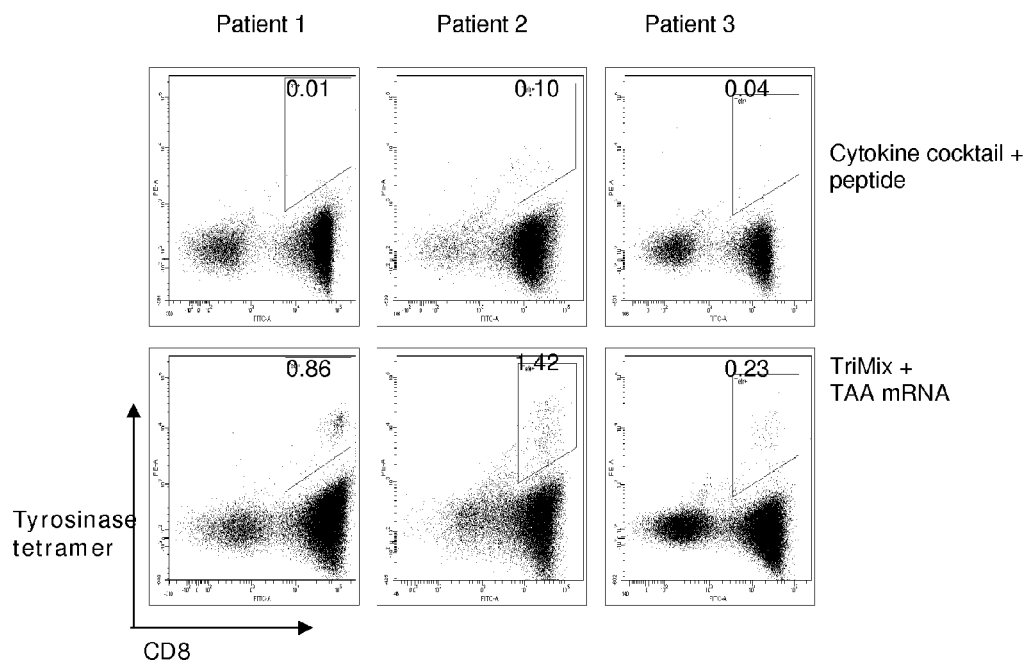
FIG. 8. Induction of CD8+ T cells specific for other antigens than MelanA in melanoma patients both in vitro and in vivo. (A) TriMix DCs as prepared for vaccination were used to stimulate CD8+ T cells isolated from the blood of HLA-A2+ melanoma patients prior to vaccination. Cytokine cocktail matured DCs pulsed with HLA-A2 restricted, Mage-A3, Mage-C2, Tyrosinase or gp100-specific peptide were used as control. After 3 weekly stimulations, the cells were stained with a panel of HLA-A2 tetramers loaded with different Mage-A3, Mage-C2, Tyrosinase or gp100-specific peptides and anti-CD8 Ab. TAA-specific CD8+ T cells were then identified by flow cytometry. Background staining with NY-ESO-1-specific HLA-A2 tetramers was subtracted. (B) Activation status and cytolytic activity of CD8+ T cells from melanoma patients before or after vaccination with TriMix DCs was determined by a CD107a/137 assay. CD8+ T cells isolated from the blood of HLA-A2+ melanoma patients before or after vaccination with TriMix DCs were stimulated 2 times in vitro with the same DCs as used for vaccination. One week after the last stimulation, cells were restimulated overnight with mature DCs electroporated with TAA mRNA or NGFR as irrelevant control in the presence of anti-CD107-PE-Cy5 mAb and Golgi-stop. Cells were harvested, stained with anti-CD8-FITC, CD137-PE and analyzed by flow cytometry. T cells were gated on FSC/SSC characteristics and CD8 positivity. The percentage of CD137/CD107a double positive cells is given. (C) Cytokine production of CD8+ T cells from melanoma patients before or after vaccination with TriMix DCs was determined by intracellular cytokine staining. CD8+ T cells isolated from the blood of HLA-A2+ melanoma patients before or after vaccination with TriMix DCs were stimulated 2 times in vitro with the same DCs as used for vaccination. One week after the last stimulation, cells were restimulated overnight with mature DCs electroporated with TAA mRNA or NGFR as irrelevant control in the presence of Golgi-plug. Then, T cells were stained for CD8, IFN-gamma and TNF-alpha positivity. T cells were gated on FSC/SSC characteristics and CD8 positivity. The percentage of IFN-gamma and/or TNF-aplha secreting cells is given.
Figure 8B:
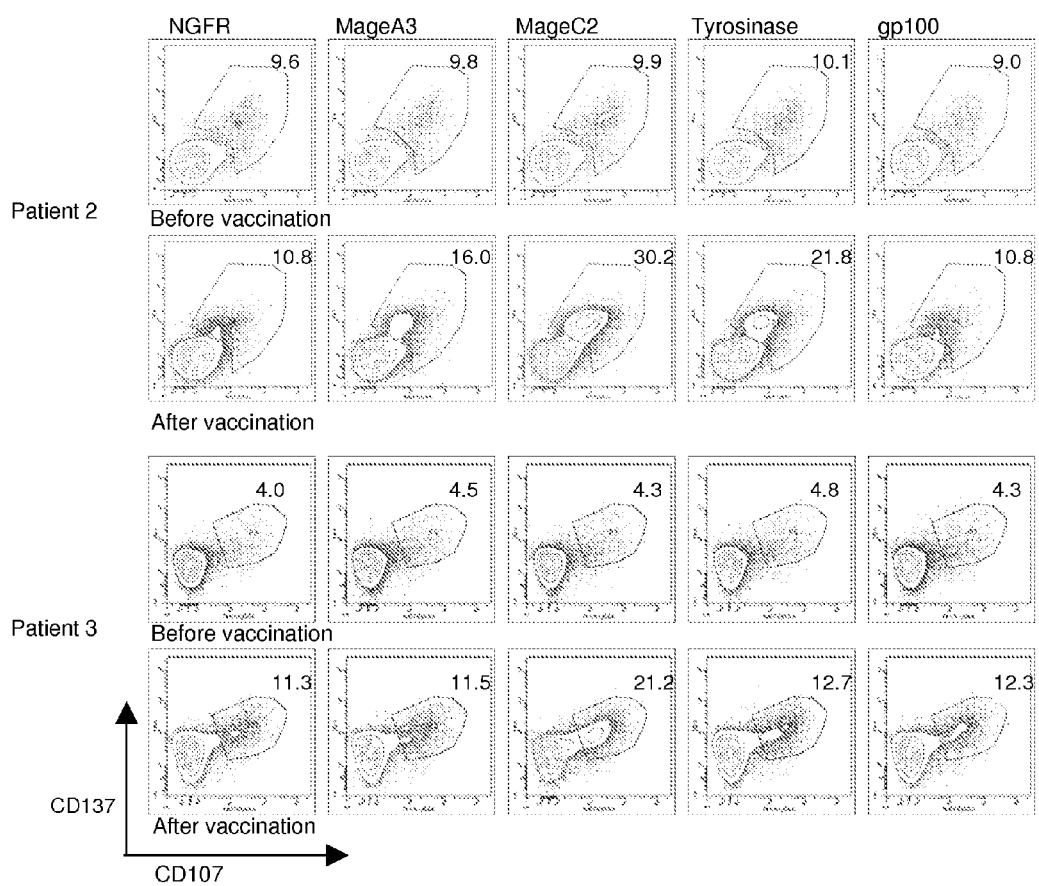

Results:

Because this work is part of the preclinical assessment of a vaccination study where TriMix DCs co-electroporated with Mage-A3, Mage-C2, Tyrosinase or gp100 mRNA will be injected into melanoma patients, we wanted to investigate whether these DCs are able to induce CD8$^+$ T cells specific for these antigens in vitro in the PBMCs of unvaccinated melanoma patients. Therefore, CD8$^+$ T cells from HLA-A2$^+$ melanoma patients were cocultured with autologous DCs as prepared for vaccination, i.e. electroporated with TriMix mRNA together with one of four tumorantigen mRNAs, and mixed afterwards at equal amounts. Cytokine cocktail matured DCs pulsed with a HLA-A2-restricted, Mage-A3, Mage-C2, Tyrosinase or gp100 derived peptide (also mixed at equal amounts) were used as controls. During the whole stimulation period, no exogenous cytokines like IL-2 or IL-7 to support T cell proliferation and survival were added. After 3 weekly stimulations, the T cells were stained with a panel of tetramers recognizing 7 different HLA-A2 restricted, Mage-A3, Mage-C2, Tyrosinase or gp100-derived epitopes. For all 3 patients tested, we observed that TriMix DCs co-electroporated with TAA mRNA were able to induce HLA-A2-restricted Tyrosinase-specific T cells, while cytokine cocktail matured DCs pulsed with the Tyrosinase-A2 peptide failed to do so (FIG. 8A). We did not observe T cells recognizing the other MageA3, Mage-C2 or gp100-specific tetramers, neither when TriMix DCs nor cytokine cocktail matured DCs were used for in vitro stimulation (data not shown). Although TriMix DCs were co-electroporated with full-length TAA mRNA encoding all possible TAA-derived epitopes, we observed no induction of other Mage-A3, Mage-C2, Tyrosinase or gp100-specific T cells, as assessed by CD137/CD107a and intracellular cytokine staining assays (FIGS. 8B and C and data not shown), although low frequencies of specific T cells might have been concealed by the aspecific T cell activation induced by TriMix DCs.

Example 8

Induction of CD8$^+$ T Cells Specific for Other Antigens than MelanA in the Blood of Melanoma Patients after Vaccination with TriMix DCs Co-Electroporated with TAA mRNA The ultimate goal of the invention is of course the provision of an anti-cancer vaccine comprising the manipulated DCs according to the invention, presenting tumor-specific antigen-derived epitope in the context of HLA class I or II molecules on their surface, that can be reintroduced into the patient, subsequently eliciting an immune response against the specific tumor marker. This immunovaccination procedure comprises the steps of (1) obtaining and manipulation of the DCs as outlined in examples 1 and 7 and (2) injecting the DCs into the subject. The subject will either be a mouse model for further analysis of the immunostimulatory effect of the vaccine in vivo, or the subject can be a cancer patient, in order to help establishing a host-mediated immune response towards the tumor-specific antigen. In short, a DC preparation preferably comprising 10-100 10$^6$ DCs, more preferably 10-50 10$^6$ DCs, resuspended in 250 µl phosphate-buffered saline (PBS), supplemented with human serum albumin is injected into the subject, preferably intradermally.

In the subject, the DCs are able to stimulate T-cells and elicit a host-mediated immune-response due to their specific immunostimulatory characteristics. The immune reaction in the host can then be analyzed through standard techniques. Analyzing the increase of inflammatory markers will point to the establishment of an immune reaction in the host, probably directed towards the tumor antigen. In order to check whether the immune response is specifically directed towards the tumor antigen presented by the DCs in the vaccine preparation, several known techniques such as intracellular staining through flow cytometry, ELISPOT or Enzyme Linked Immuno-Sorbent Assays (ELISA), using peptide fragments of the tumor antigen or the whole tumor antigen in order to capture and detect tumor-antigen specific host T cells can be used. The immune response can be monitored both in the peripheral blood of the patient or in the skin, after induction of a delayed type hypersensitivity (DTH)-reaction and subsequent biopsy of the DTH region.

Patients, Vaccine Preparation and Vaccination Schedule.

Three HLA-A2$^+$ patients (2M/1F) with recurrent stage III or stage 1V melanoma were recruited in an ongoing institutional (UZ Brussel) pilot trial with autologous TriMix-DC vaccine for patients with advanced melanoma. For vaccination purposes, DCs were electroporated with mRNA encoding one of four tumorantigens (Mage-A3, Mage-C2, Tyrosinase and gp100) and the TriMix-mRNA. After a rest period of one hour, the cells are mixed at equal ratios. The first vaccine was administered prior to cryopreservation of the DC-caccine, subsequent vaccines were performed with cells that were thawed at the day of vaccination. Vaccines consist of ±12.5 10$^6$ TriMix DC per antigen and are administered by 4 bi-weekly intradermal injections at 4 different injection sites (axillar and/or inguinal region).

Figure 8C:
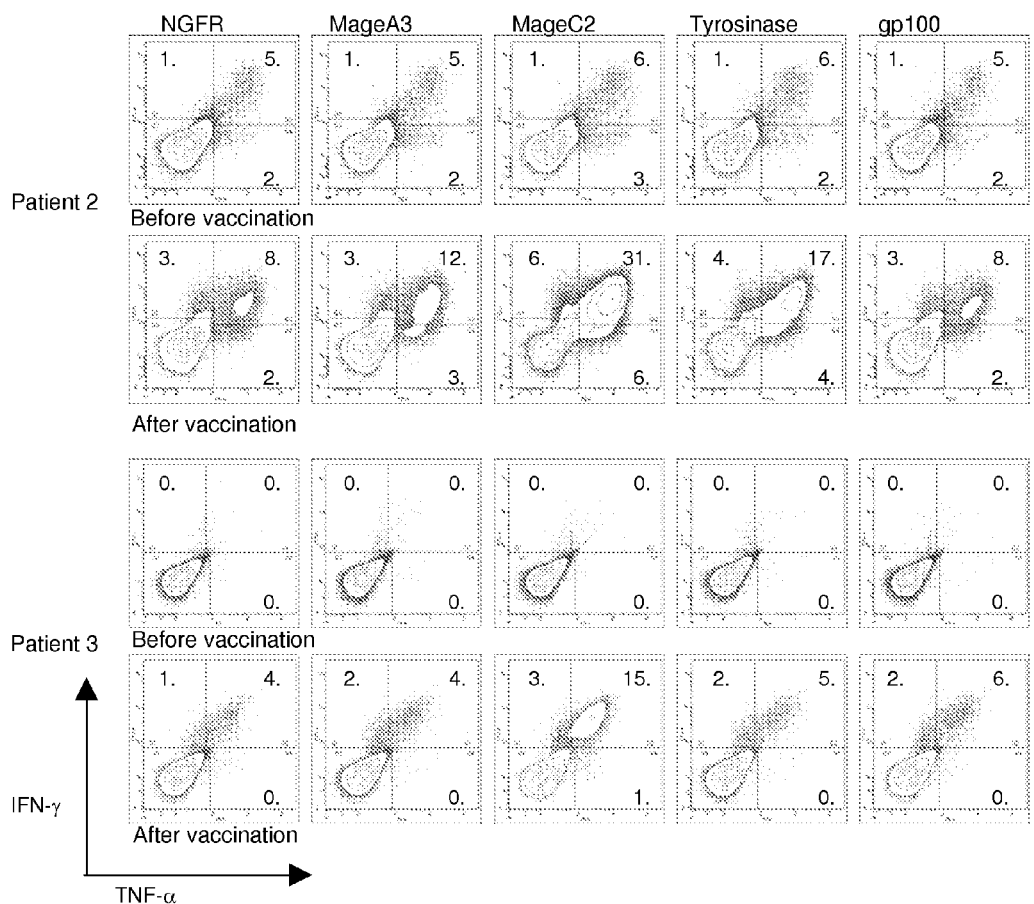

We investigated whether TriMix DCs co-electroporated with Mage-A3, Mage-C2, Tyrosinase or gp100 mRNA would be able to induce an antigen-specific CD8$^+$ T cell-response in vivo. Therefore, 2 HLA-A2$^+$ melanoma patients (patients 2 and 3) were vaccinated 4 times at bi-weekly intervals with TriMix DCs. Two weeks after the last vaccination, CD8$^+$ T cells isolated from the blood of these patients were restimulated in vitro with autologous DCs, either with TriMix DCs as prepared for vaccination or with cytokine cocktail matured DCs co-electroporated with tumorantigen mRNA. Again, during the whole stimulation period, no exogenous cytokines were added. After 2 weekly stimulations, the antigen-specificity and functionality of the T cells was investigated by staining with the HLA-A2 tetramer panel and by the CD137/CD107a and intracellular cytokine staining assays; and this was compared to the response induced in the CD8$^+$ T cells of the same patients, but before vaccination. For both patients, we observed no T cells specific for the known HLA-A2 restricted, Mage-A3, Mage-C2, Tyrosinase or gp100-derived epitopes in tetramer staining (data not shown), although we had been able to induce Tyrosinase-A2 specific T cells in the CD8+ T cells of these same patients before vaccination (FIG. 8A). This was still the case after the T cells had received an extra stimulation round in vitro (data not shown). Because the patients were vaccinated with DCs co-electroporated with full-length tumorantigen mRNA encoding all possible tumorantigen-derived epitopes, we investigated whether a T cell response specific for other epitopes than the known HLA-A2 restricted epitopes had been induced. Therefore, one week after the second restimulation in vitro, T cells were restimulated overnight with mature DCs electroporated with tumorantigen mRNA or NGFR as irrelevant control after which a CD137/CD107a (FIG. 8B) and an intracellular cytokine staining assay (FIG. 8C) were performed. Indeed, we observed strong, vaccine-induced responses against other Mage-A3 (patient 2), Mage-C2 (patient 2 and 3) and Tyrosinase-epitopes (patient 2), which were not present before vaccination. Overall, similar results were obtained when TriMix or cytokine cocktail matured DCs were used for restimulation in vitro, except for the fact that the latter induced less aspecific T cells (data not shown).

Example 9

Combining the Different mRNAs Encoding Immunostimulatory Factors in a Single mRNA Molecule for Electroporation For transfection of 2 or more mRNA or DNA molecules encoding functional immunostimulatory factors and/or factors inhibiting inhibitory molecules, separate mRNA or DNA preparations can be used as is shown in the above examples. In this case, each single factor is encoded by one single mRNA or DNA molecule. In this alternative example, several factors are linked to each other by means of an IRES (internal ribosomal entry site) sequence or a cleavable 2a peptide-encoding sequence. This way, two or more factors can be encoded by one single mRNA or DNA molecule. Preliminary data where cells were electroporated with mRNA encoding CD40L and CD70 linked by an IRES sequence or a cleavable 2a peptide show that this approach is indeed feasible. Extrapolation of this system to more than two immunostimulatory factors is of course also anticipated by this example.

What is claimed is:

1. A composition for improving the immunostimulatory characteristics of dendritic cells (DCs) comprising a combination of mRNA molecules encoding functional immunostimulatory proteins CD40L, CD70, and constitutively active TLR4.

2. The composition of claim 1, wherein said mRNA molecules encoding the immunostimulatory proteins are part of a single mRNA molecule.

3. The composition of claim 2, wherein the single mRNA molecule is capable of expressing the proteins simultaneously.

4. The composition of claim 3, wherein the mRNA molecules encoding the immunostimulatory proteins are separated in the single mRNA molecule by an internal ribosomal entry site (IRES) or a self-cleaving 2a peptide encoding sequence.

5. The composition of claim 1, additionally comprising one or more mRNA or DNA molecules encoding functional immunostimulatory proteins selected from the group consisting of: IL-12p70, EL-selectin, CCR7, 4-1BBL, and combinations thereof.

6. The composition of claim 1, additionally comprising a target-specific antigen selected from the group consisting of: total mRNA isolated from (a) target cell(s), one or more specific target mRNA molecules, protein lysates of (a) target cell(s), specific proteins from (a) target cell(s), or a synthetic target-specific peptide or protein and synthetic mRNA or DNA encoding a target specific antigen or its derived peptide(s).

7. A method for improving the immunostimulatory characteristics of dendritic cells comprising contacting the dendritic cells with the composition of claim 1 in vitro and introducing the mRNA molecules into dendritic cells.

8. The method of claim 1 wherein the dendritic cells are additionally stimulated with soluble factors selected from TLR ligands, IFN-gamma, TNF-alpha, IL-6, IL-1 beta and/or PGE2.

9. The method of claim 1, wherein the introduction of mRNA molecules is obtained via a method selected from the group consisting of electroporation, viral transduction, lipofection and transfection.

* * * * *

UNITED STATES PATENT AND TRADEMARK OFFICE
CERTIFICATE OF CORRECTION

PATENT NO.       : 8,476,419 B2                    Page 1 of 1
APPLICATION NO.  : 12/677476
DATED            : July 2, 2013
INVENTOR(S)      : Thielemans et al.

It is certified that error appears in the above-identified patent and that said Letters Patent is hereby corrected as shown below:

In the Specification

In column 8 at line 9, Change "aplha" to --alpha--.

In column 9 at line 18, Change "Eethyma, -Encephalitis" to --Erthyma,--.

In column 10 at line 40, Change "were" to --where--.

In column 17 at line 51, Change "concommitant" to --concomitant--.

In column 18 at line 4, Change "concommitant" to --concomitant--.

In column 21 at line 21, Change "pcDNA3" to --pCDNA3--.

In column 32 at line 34, Change "1V" to --IV--.

Signed and Sealed this
Seventh Day of January, 2014

Margaret A. Focarino
*Commissioner for Patents of the United States Patent and Trademark Office*